United States Patent

Malecha et al.

(10) Patent No.: US 9,459,232 B2
(45) Date of Patent: Oct. 4, 2016

(54) METHOD AND SYSTEM TO DETERMINE ERRONEOUS MEASUREMENT SIGNALS DURING A TEST MEASUREMENT SEQUENCE

(71) Applicant: LifeScan Scotland Limited, Iverness-shire (GB)

(72) Inventors: Michael Malecha, Muir of Ord (GB); Alexander Strachan, Moray (GB); Yeswanth Gadde, Inverness (GB)

(73) Assignee: LifeScan Scotland Limited, Inverness (GB)

( * ) Notice: Subject to any disclaimer, the term of this patent is extended or adjusted under 35 U.S.C. 154(b) by 503 days.

(21) Appl. No.: 14/018,910

(22) Filed: Sep. 5, 2013

(65) Prior Publication Data

US 2015/0060300 A1 Mar. 5, 2015

(51) Int. Cl.
*G01N 27/327* (2006.01)

(52) U.S. Cl.
CPC ...... *G01N 27/3275* (2013.01); *G01N 27/3274* (2013.01)

(58) Field of Classification Search
CPC .................................. G01N 27/327–27/3274
See application file for complete search history.

(56) References Cited

U.S. PATENT DOCUMENTS 5,352,351 A  10/1994 White et al.
2006/0224658 A1  10/2006 Sato et al.

FOREIGN PATENT DOCUMENTS

WO  WO 2013/098563 A1  7/2013
WO  WO 2013/098564 A1  7/2013
WO  WO 2013/098565 A1  7/2013

OTHER PUBLICATIONS

Application as filed for related U.S. Appl. No. 61/581,087, filed Dec. 29, 2011.
Application as filed for related U.S. Appl. No. 61/581,089, filed Dec. 29, 2011.
Application as filed for related U.S. Appl. No. 61/581,099, filed Dec. 29, 2011.
Application as filed for related U.S. Appl. No. 61/581,100, filed Dec. 29, 2011.
Application as filed for related U.S. Appl. No. 61/654,013, filed May 31, 2012.
International Search Report and Written Opinion issued in related International Patent Application No. PCT/EP2014/068819, dated Oct. 31, 2014, 12 pages.

*Primary Examiner* — Alexander Noguerola

(57) ABSTRACT

Various embodiments that allow a more accurate electrochemical test strip measurement by identifying erroneous output signals during a glucose measurement thereby ensuring a much more accurate glucose test system.

12 Claims, 16 Drawing Sheets

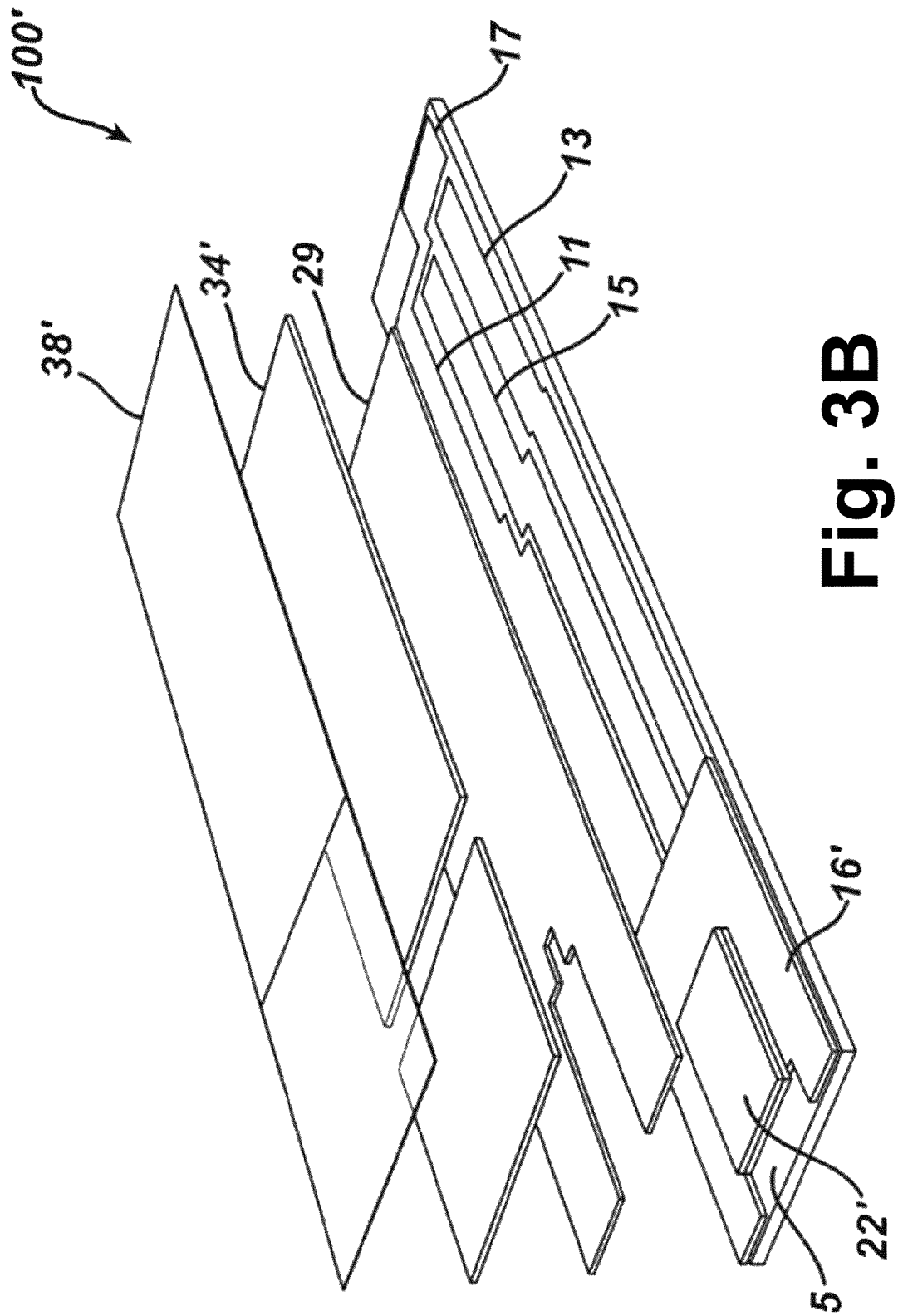

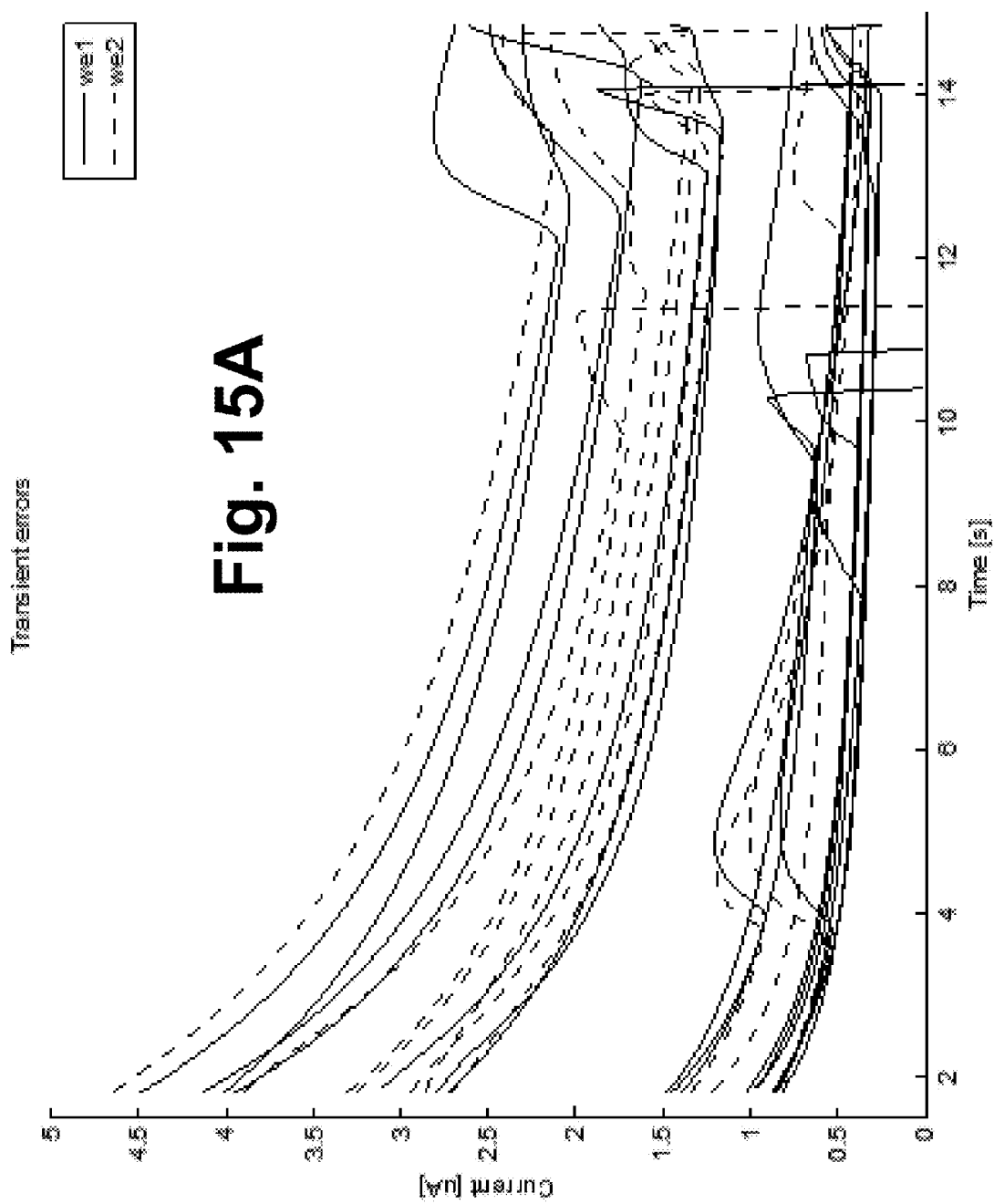

METHOD AND SYSTEM TO DETERMINE ERRONEOUS MEASUREMENT SIGNALS DURING A TEST MEASUREMENT SEQUENCE

BACKGROUND

Electrochemical glucose test strips, such as those used in the OneTouch® Ultra® whole blood testing kit, which is available from LifeScan, Inc., are designed to measure the concentration of glucose in a blood sample from patients with diabetes. The measurement of glucose can be based on the selective oxidation of glucose by the enzyme glucose oxidase (GO). The reactions that can occur in a glucose test strip are summarized below in Equations 1 and 2.e

Eq. 1

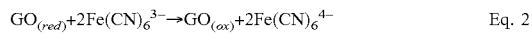

Eq. 2

As illustrated in Equation 1, glucose is oxidized to gluconic acid by the oxidized form of glucose oxidase ($GO_{(ox)}$). It should be noted that $GO_{(ox)}$ may also be referred to as an "oxidized enzyme." During the reaction in Equation 1, the oxidized enzyme $GO_{(ox)}$ is converted to its reduced state, which is denoted as $GO_{(red)}$ (i.e., "reduced enzyme"). Next, the reduced enzyme $GO_{(red)}$ is re-oxidized back to $GO_{(ox)}$ by reaction with $Fe(CN)_6^{3-}$ (referred to as either the oxidized mediator or ferricyanide) as illustrated in Equation 2. During the re-generation of $GO_{(red)}$ back to its oxidized state $GO_{(ox)}$, $Fe(CN)_6^{3-}$ is reduced to $Fe(CN)_6^{4-}$ (referred to as either reduced mediator or ferrocyanide).

When the reactions set forth above are conducted with a test voltage applied between two electrodes, a test output signal can be created by the electrochemical re-oxidation of the reduced mediator at the electrode surface. Thus, since, in an ideal environment, the amount of ferrocyanide created during the chemical reaction described above is directly proportional to the amount of glucose in the sample positioned between the electrodes, the test output signal generated would be proportional to the glucose content of the sample. A mediator, such as ferricyanide, is a compound that accepts electrons from an enzyme such as glucose oxidase and then donates the electrons to an electrode. As the concentration of glucose in the sample increases, the amount of reduced mediator formed also increases; hence, there is a direct relationship between the test output signal, resulting from the re-oxidation of reduced mediator, and glucose concentration. In particular, the transfer of electrons across the electrical interface results in the flow of a test output signal (2 moles of electrons for every mole of glucose that is oxidized). The test output signal resulting from the introduction of glucose can, therefore, be referred to as a glucose output signal.

Because it can be very important to know the concentration of glucose in blood, particularly in people with diabetes, test meters have been developed using the principals set forth above to enable the average person to sample and test their blood for determining their glucose concentration at any given time. The glucose output signal generated is detected by the test meter and converted into a glucose concentration reading using an algorithm that relates the test output signal to a glucose concentration via a simple mathematical formula. In general, the test meters work in conjunction with a disposable test strip that may include a sample-receiving chamber and at least two electrodes disposed within the sample-receiving chamber in addition to the enzyme (e.g. glucose oxidase) and the mediator (e.g. ferricyanide). In use, the user pricks their finger or other convenient site to induce bleeding and introduces a blood sample to the sample-receiving chamber, thus starting the chemical reaction set forth above.

SUMMARY OF THE DISCLOSURE

In one aspect, applicants have devised a glucose measurement system that includes a biosensor and a meter. The biosensor has a plurality of electrodes including at least two electrodes with an enzyme disposed thereon. The meter includes a microcontroller coupled to a power source, memory and the plurality of electrodes of the biosensor. The microcontroller is configured to: drive a signal to the at least two electrodes when a fluid sample with an glucose is deposited proximate the at least two electrodes to start a test measurement sequence for an electrochemical reaction of the glucose in the fluid sample with the enzyme; measure an output signal(I(t)) from at least one electrode during the electrochemical reaction over a series of time instances to obtain a magnitude of the output signal for each time instance (t); determine an output differential as a difference in the respective magnitudes of the output signal for at least two consecutive time instances (t and t+1) within a predetermined time window (c to d) during the test measurement sequence; if the output differential is greater than zero then (1) increment a first index (x) by one and (2) set a second index (y) value as equal to the sum of a previous value of the second index (y) and the output differential and if the first index (x) is greater or equal to a first threshold (a) and a second index (y) is greater than a second threshold (b) then annunciate an error otherwise calculate the glucose value from the output signal and annunciate the glucose value.

In yet a further aspect, applicants have also devised a method of determining a glucose value from a fluid sample with a biosensor and a glucose meter. The biosensor has at least two electrodes and reagent disposed thereon. The glucose meter has a microcontroller configured to connect to the biosensor and to a memory and a power source. The method can be achieved by: initiating a start of a test measurement sequence upon deposition of a fluid sample proximate the at least two electrodes of the biosensor; applying an input signal to the fluid sample to cause a transformation of glucose into an enzymatic by-product; measuring output signal transient from the fluid sample over a predetermined time window from the start of the test sequence, the measuring including sampling an output signal from at least one electrode during the electrochemical reaction over a series of time instances (I(t)) to obtain a magnitude of the output signal for each time instance (t); determining an output differential as a difference in the respective magnitudes of the output signal for at least two consecutive time instances (t and t+1) within the predetermined time window (c to d) during the test measurement sequence; if the output differential is greater than zero then: (1) incrementing a first index (x) by one and (2) setting a second index (y) value as equal to the sum of a previous value of the second index (y) and the output differential (ΔI); and if the first index (x) is greater or equal to a first threshold (a) and a second index (y) is greater than a second threshold (b) then annunciating an error, otherwise calculating a glucose value of the fluid sample and annunciating the glucose value.

And for these aspects, the following features may also be utilized in various combinations with these previously disclosed aspects: the predetermined time window may include from about 1 second after a start of a test sequence to about 8 seconds after the start of the test sequence; in which the first threshold (a) may include about 5 and the second threshold (b) may include about 300; the predetermined time window may include from about 2 second after a start of a test sequence to about 8 seconds after the start of the test sequence; the first threshold (a) may include about 5 and the second threshold (b) may include about 150; the predetermined time window may include from about 1 second after a start of a test sequence to about 8 seconds after the start of the test sequence; and the calculating of the glucose value may include measuring a magnitude of the output signal proximate a predetermined time instance from the start of the test sequence and deriving the glucose value from a first calibration value and a second calibration value; the deriving may include utilizing an equation of the form $$G=[I-\text{Intercept}]/\text{Slope}$$

Where

G includes a glucose value;

I includes a summation of the magnitude of the signals measured from each of the electrodes proximate a predetermined time instance;

Slope includes a value obtained from calibration testing of a batch of test strip of which this particular strip comes from;

Intercept includes a value obtained from calibration testing of a batch of test strip of which this particular strip comes from.

These and other embodiments, features and advantages will become apparent to those skilled in the art when taken with reference to the following more detailed description of the exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements), in which:

FIG. 3B illustrates in perspective view for an alternate test strip 100' for the system of FIG. 1.

FIG. 15A shows the some of the erroneous output signal transients identified by our inventive technique.

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment. As used herein, "oscillating signal" includes voltage signal(s) or current signal(s) that, respectively, change polarity or alternate direction of current or are multi-directional. Also used herein, the phrase "electrical signal" or "signal" is intended to include direct current signal, alternating signal or any signal within the electromagnetic spectrum. The terms "processor"; "microprocessor"; or "microcontroller" are intended to have the same meaning and are intended to be used interchangeably.

Figure 1:
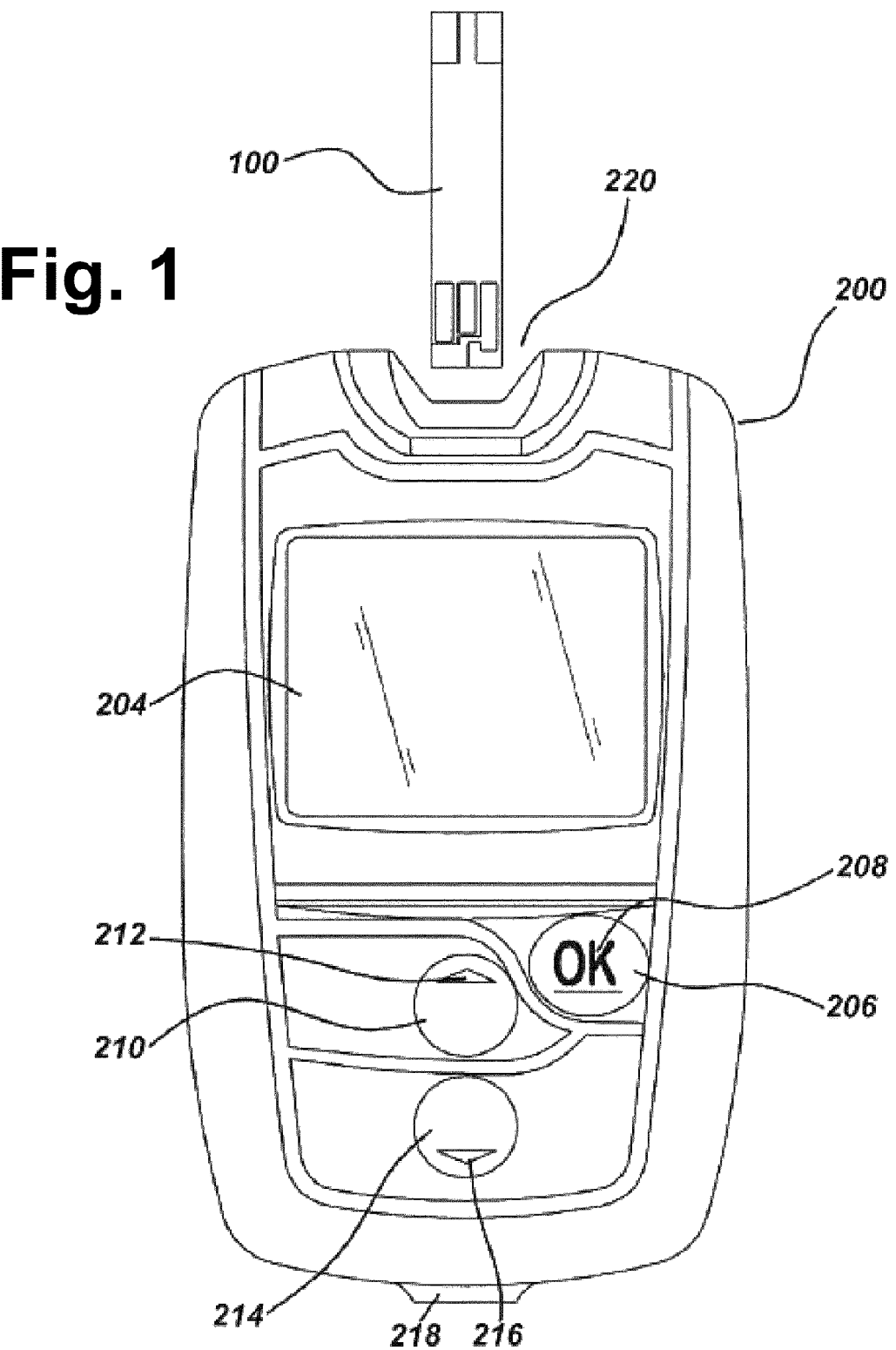
FIG. 1 illustrates a glucose measurement system.

FIG. 1 illustrates a glucose measurement system having test strip 100 and test meter 200, for testing glucose levels in the blood of an individual with methods and techniques illustrated and described herein. Test meter 200 may include user interface inputs (206, 210, 214), which can be in the form of buttons, for entry of data, navigation of menus, and execution of commands. Data can include values representative of analyte concentration, and/or information that are related to the everyday lifestyle of an individual. Information, which is related to the everyday lifestyle, can include food intake, medication use, the occurrence of health check-ups, general health condition and exercise levels of an individual. Test meter 200 can also include a display 204 that can be used to report measured glucose levels, and to facilitate entry of lifestyle related information.

Test meter 200 may include a first user interface input 206, a second user interface input 210, and a third user interface input 214. User interface inputs 206, 210, and 214 facilitate entry and analysis of data stored in the testing device, enabling a user to navigate through the user interface displayed on display 204. User interface inputs 206, 210, and 214 include a first marking 208, a second marking 212, and a third marking 216, which help in correlating user interface inputs to characters on display 204.

Test meter 200 can be turned on by inserting a test strip 100 into a strip port connector 220, by pressing and briefly holding first user interface input 206, or by the detection of data traffic across a data port 218. Test meter 200 can be switched off by removing test strip 100, pressing and briefly holding first user interface input 206, navigating to and selecting a meter off option from a main menu screen, or by not pressing any buttons for a predetermined time. Display 204 can optionally include a backlight.

In one embodiment, test meter 200 can be configured to not receive a calibration input for example, from any external source, when switching from a first test strip batch to a second test strip batch. Thus, in one exemplary embodiment, the meter is configured to not receive a calibration input from external sources, such as a user interface (such as inputs 206, 210, 214), an inserted test strip, a separate code key or a code strip, data port 218. Such a calibration input is not necessary when all of the test strip batches have a substantially uniform calibration characteristic. The calibration input can be a set of values ascribed to a particular test strip batch. For example, the calibration input can include a batch slope and a batch intercept value for a particular test strip batch. The calibrations input, such as batch slope and intercept values, may be preset within the meter as will be described below.

Figure 2:
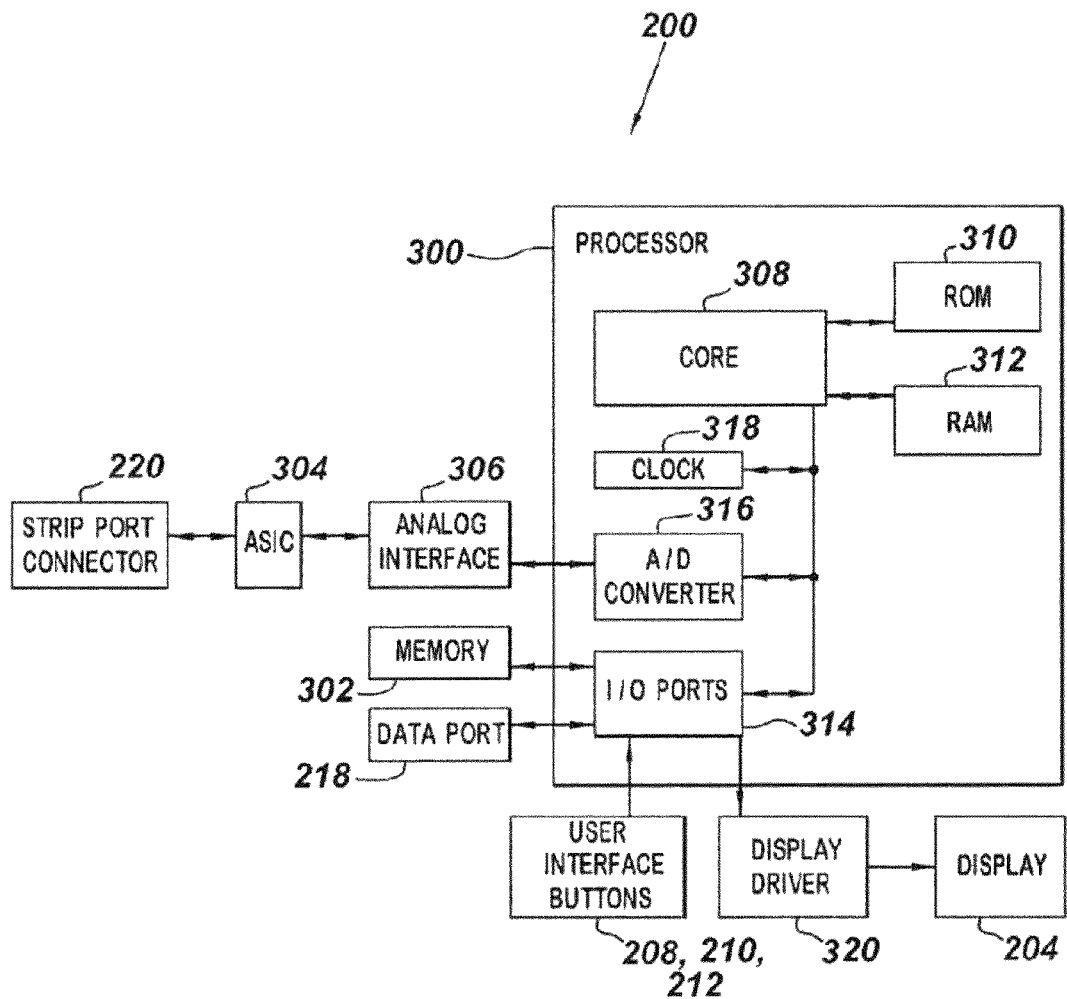
FIG. 2 illustrates in simplified schematic form the components of the meter 200.

Referring to FIG. 2, an exemplary internal layout of test meter 200 is shown. Test meter 200 may include a processor 300, which in some embodiments described and illustrated herein is a 32-bit RISC microcontroller. In the preferred embodiments described and illustrated herein, processor 300 is preferably selected from the MSP 430 family of ultra-low power microcontrollers manufactured by Texas Instruments of Dallas, Tex. The processor can be bi-directionally connected via I/O ports 314 to a memory 302, which in some embodiments described and illustrated herein is an EEPROM. Also connected to processor 300 via I/O ports 214 are the data port 218, the user interface inputs 206, 210, and 214, and a display driver 320. Data port 218 can be connected to processor 300, thereby enabling transfer of data between memory 302 and an external device, such as a personal computer. User interface inputs 206, 210, and 214 are directly connected to processor 300. Processor 300 controls display 204 via display driver 320. Memory 302 may be pre-loaded with calibration information, such as batch slope and batch intercept values, during production of test meter 200. This pre-loaded calibration information can be accessed and used by processor 300 upon receiving a suitable signal (such as current) from the strip via strip port connector 220 so as to calculate a corresponding analyte level (such as blood glucose concentration) using the signal and the calibration information without receiving calibration input from any external source.

In embodiments described and illustrated herein, test meter 200 may include an Application Specific Integrated Circuit (ASIC) 304, so as to provide electronic circuitry used in measurements of glucose level in blood that has been applied to a test strip 100 inserted into strip port connector 220. Analog voltages can pass to and from ASIC 304 by way of an analog interface 306. Analog signals from analog interface 306 can be converted to digital signals by an A/D converter 316. Processor 300 further includes a core 308, a ROM 310 (containing computer code), a RAM 312, and a clock 318. In one embodiment, the processor 300 is configured (or programmed) to disable all of the user interface inputs except for a single input upon a display of an analyte value by the display unit such as, for example, during a time period after an analyte measurement. In an alternative embodiment, the processor 300 is configured (or programmed) to ignore any input from all of the user interface inputs except for a single input upon a display of an analyte value by the display unit.

Figure 3A:
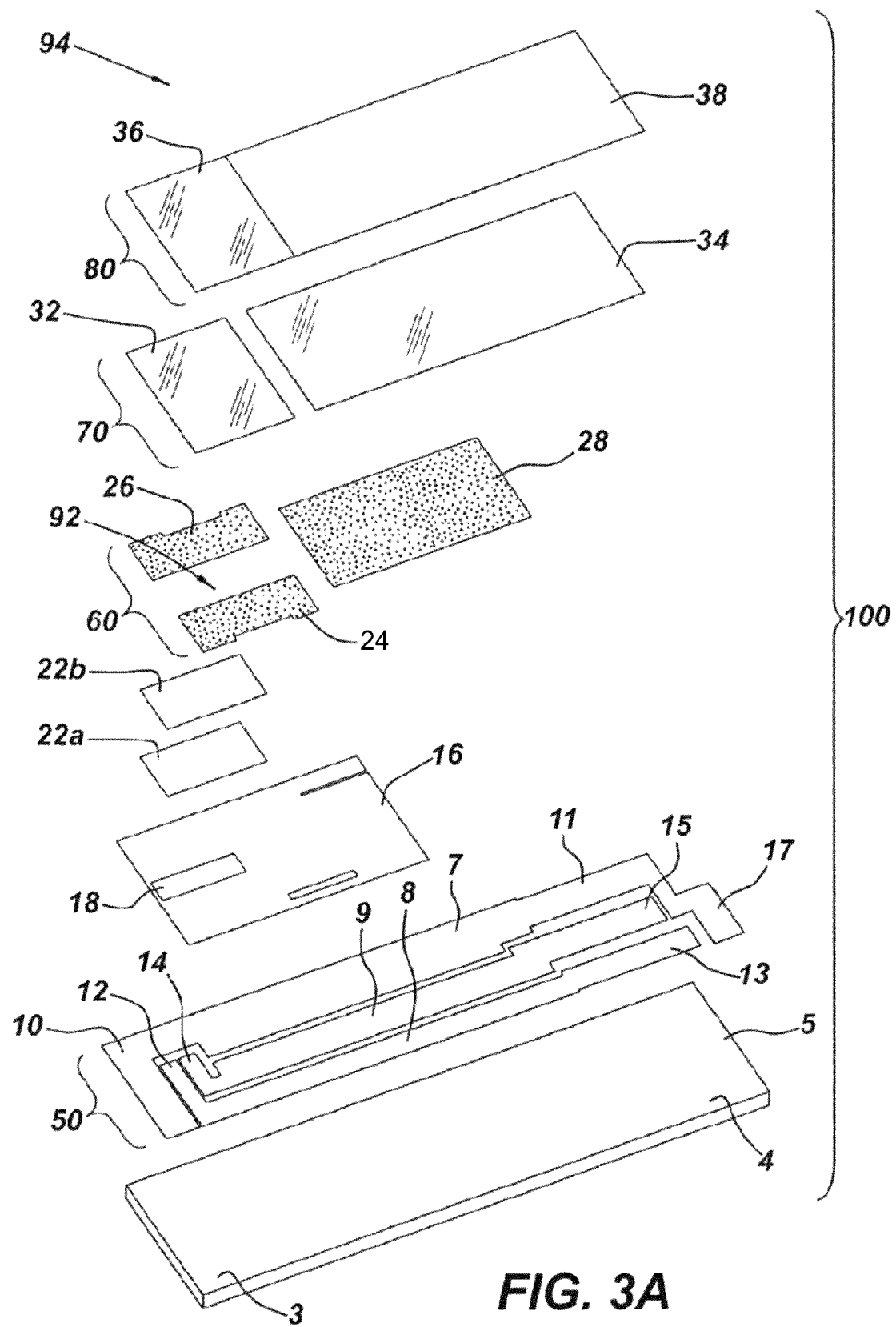
FIG. 3A illustrates the test strip 100 of the system of FIG. 1.

FIG. 3A is an exemplary exploded perspective view of a test strip 100, which may include seven layers disposed on a substrate 5. The seven layers disposed on substrate 5 can be a conductive layer 50 (which can also be referred to as electrode layer 50), an insulation layer 16, two overlapping reagent layers 22a and 22b, an adhesive layer 60 which includes adhesive portions 24, 26, and 28, a hydrophilic layer 70, and a top layer 80. Test strip 100 may be manufactured in a series of steps where the conductive layer 50, insulation layer 16, reagent layers 22, adhesive layer 60 are sequentially deposited on substrate 5 using, for example, a screen-printing process. Hydrophilic layer 70 and top layer 80 can be disposed from a roll stock and laminated onto substrate 5 as either an integrated laminate or as separate layers. Test strip 100 has a distal portion 3 and a proximal portion 4 as shown in FIG. 3A.

Test strip 100 may include a sample-receiving chamber 92 through which a blood sample may be drawn. Sample-receiving chamber 92 can include an inlet at a proximal end and an outlet at the side edges of test strip 100, as illustrated in FIG. 3A. A blood sample 94 can be applied to the inlet to fill a sample-receiving chamber 92 so that glucose can be measured. The side edges of a first adhesive pad 24 and a second adhesive pad 26 located adjacent to reagent layer 22 each define a wall of sample-receiving chamber 92, as illustrated in FIG. 3A. A bottom portion or "floor" of sample-receiving chamber 92 may include a portion of substrate 5, conductive layer 50, and insulation layer 16, as illustrated in FIG. 3A. A top portion or "roof" of sample-receiving chamber 92 may include distal hydrophilic portion 32, as illustrated in FIG. 3A.

For test strip 100, as illustrated in FIG. 3A, substrate 5 can be used as a foundation for helping support subsequently applied layers. Substrate 5 can be in the form of a polyester sheet such as a polyethylene tetraphthalate (PET) material (Hostaphan PET supplied by Mitsubishi). Substrate 5 can be in a roll format, nominally 350 microns thick by 370 millimeters wide and approximately 60 meters in length.

A conductive layer is required for forming electrodes that can be used for the electrochemical measurement of glucose. Conductive layer 50 can be made from a carbon ink that is screen-printed onto substrate 5. In a screen-printing process, carbon ink is loaded onto a screen and then transferred through the screen using a squeegee. The printed carbon ink can be dried using hot air at about 140° C. The carbon ink can include VAGH resin, carbon black, graphite (KS 15), and one or more solvents for the resin, carbon and graphite mixture. More particularly, the carbon ink may incorporate a ratio of carbon black:VAGH resin of about 2.90:1 and a ratio of graphite:carbon black of about 2.62:1 in the carbon ink.

For test strip 100, as illustrated in FIG. 3A, conductive layer 50 may include a reference electrode 10, a first working electrode 12, a second working electrode 14, a first contact pad 13, a second contact pad 15, a reference contact pad 11, a first working electrode track 8, a second working electrode track 9, a reference electrode track 7, and a strip detection bar 17. The conductive layer may be formed from carbon ink. First contact pad 13, second contact pad 15, and reference contact pad 11 may be adapted to electrically connect to a test meter. First working electrode track 8 provides an electrically continuous pathway from first working electrode 12 to first contact pad 13. Similarly, second working electrode track 9 provides an electrically continuous pathway from second working electrode 14 to second contact pad 15. Similarly, reference electrode track 7 provides an electrically continuous pathway from reference electrode 10 to reference contact pad 11. Strip detection bar 17 is electrically connected to reference contact pad 11. A test meter can detect that test strip 100 has been properly inserted by measuring a continuity between reference contact pad 11 and strip detection bar 17, as illustrated in FIG. 3A.

An alternate version of the test strip 100 is shown in FIG. 3B as strip 100'. In this version, the top layer 38', hydrophilic film layer 34' and spacer 29 have been combined together to form an integrated assembly for mounting to the substrate 5 with reagent layer 22' disposed proximate insulation layer 16'.

Figure 4A:
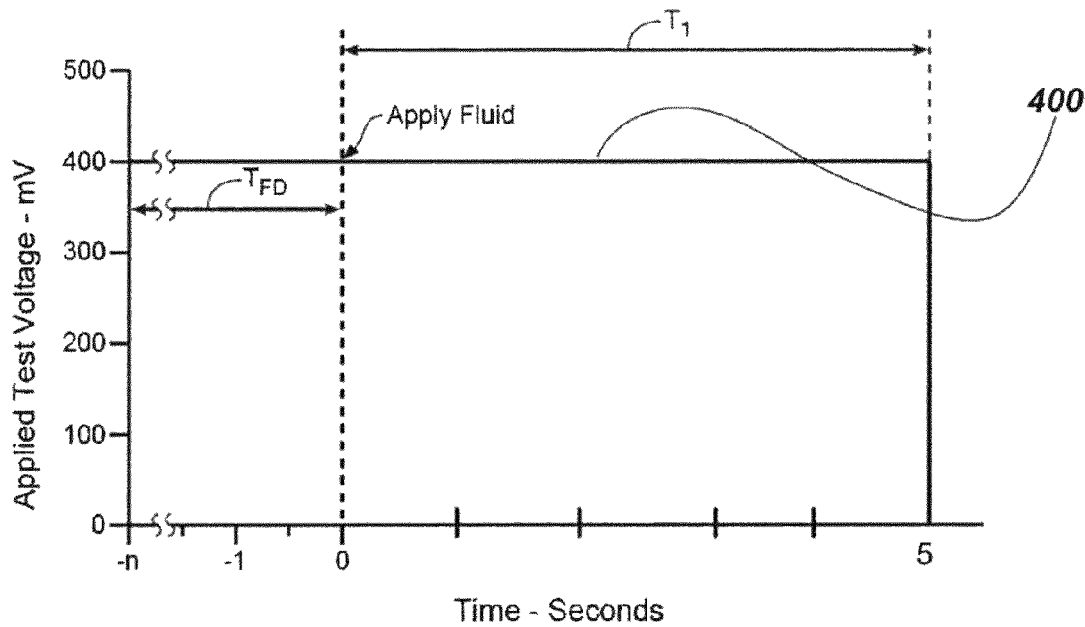
FIG. 4A illustrates a graph of time over applied potential to the test strip of FIG. 1.

FIG. 4A is an exemplary chart of a test voltage applied to test strip 100. Before a fluid sample is applied to test strip 100, test meter 200 is in a fluid detection mode in which a first test voltage of about 400 millivolts is applied between second working electrode 14 and reference electrode 10. A second test voltage of about 400 millivolts is preferably applied simultaneously between first working electrode 12 and reference electrode 10. Alternatively, the second test voltage may also be applied contemporaneously such that a time interval of the application of the first test voltage overlaps with a time interval in the application of the second test voltage. The test meter may be in a fluid detection mode during fluid detection time interval $t_{FD}$ prior to the detection of physiological fluid at starting time at zero. In the fluid detection mode, test meter 200 determines when a fluid is applied to test strip 100 such that the fluid wets second working electrode 14 and reference electrode 10. Once test meter 200 recognizes that the physiological fluid has been applied because of, for example, a sufficient increase in the measured test output signal at second working electrode 14, test meter 200 assigns a zero second marker at zero time "0" and starts the test time interval $T_1$. Upon the completion of the test time interval $T_1$, the test voltage is removed. For simplicity, FIG. 4A only shows the first test voltage applied to test strip 100.

Hereafter, a description of how glucose concentration is determined from the known output signal transients (i.e., the measured electrical output signal response in nanoamperes as a function of time) that are measured when the test voltages of FIG. 4A are applied to the known test strip 100.

In FIG. 4A, the first and second test voltages applied to test strip 100 are generally from about +100 millivolts to about +600 millivolts. In one embodiment in which the electrodes include carbon ink and the mediator is ferricyanide, the test voltage is about +400 millivolts. Other mediator and electrode material combinations will require different test voltages. The duration of the test voltages is generally from about 2 to about 4 seconds after a reaction period and is typically about 3 seconds after a reaction period. Typically, time $T_1$ is measured relative to time $t_0$. As the voltage 400 is maintained in FIG. 4A for the duration of T1, the output signal transient 402 for the first working electrode is generated starting at zero time and likewise the output signal transient 404 for the second working electrode is also generated with respect to the zero time in FIG. 4B. The output signals 402 and 404 (from respective working electrodes) are measured or sampled over time instances "t" such that for the preferred embodiments, there are approximately 200 measurements (or sampling intervals). The output signal transients build up to a peak proximate peak time at which time, the output signal slowly drops off until approximately 5 seconds after zero time. At the point 406, the output signal magnitude for each of the working electrodes are measured and added together. From knowledge of the calibration code offset and slope for the particular test strip 100, the glucose concentration can be calculated. "Intercept" and "Slope" are the values obtained by measuring calibration data from a batch of test strips. Typically around 1500 strips are selected at random from the lot or batch. Body fluid from donors is spiked to various analyte levels, typically six different glucose concentrations. Typically, blood from 12 different donors is spiked to each of the six levels. Eight strips are given blood from identical donors and levels so that a total of 12×6×8=576 tests are conducted for that lot. These are benchmarked against actual analyte level (e.g., blood glucose concentration) by measuring these using a standard laboratory analyzer such as Yellow Springs Instrument (YSI). A graph of measured glucose concentration is plotted against actual glucose concentration (or measured current versus YSI current) and a formula y=mx+c least squares fitted to the graph to give a value for batch slope m and batch intercept c for the remaining strips from the lot or batch.

Figure 4B:
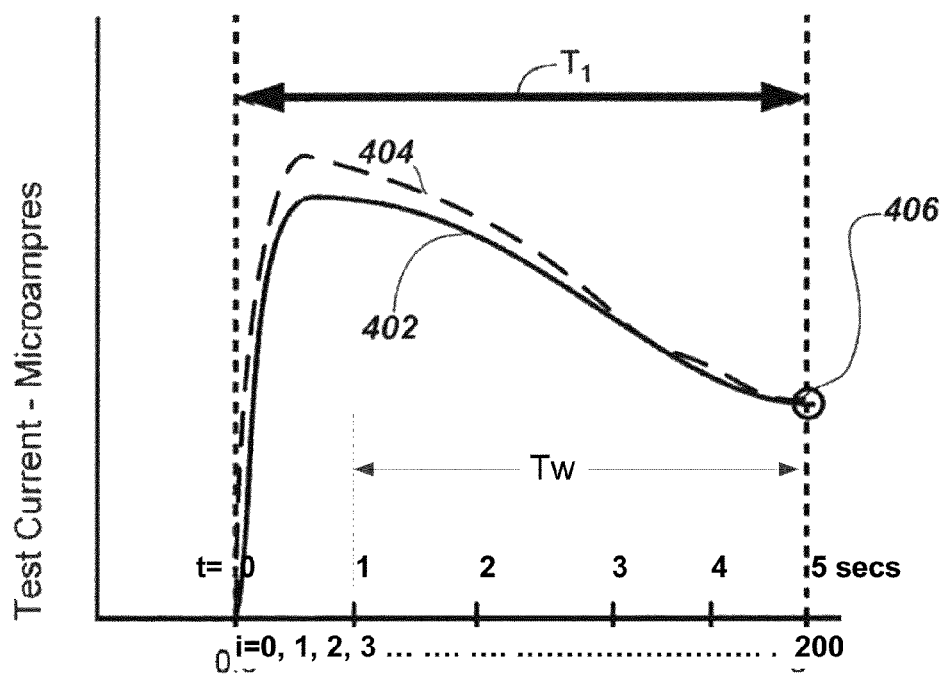
FIG. 4B illustrates a graph of time over output current from the test strip of FIG. 1.

As an example of an analyte calculation (e.g., glucose) for strip 100 (FIG. 3A), it is assumed in FIG. 4B that the sampled output signal value at 406 for the first working electrode is 1600 nanoamps whereas the current value at 406 for the second working electrode is 1300 nanoamps and for the calibration code of the test strip the Intercept is 500 nanoamps and the Slope is 18 nanoamp/mg/dL. Glucose concentration G can be thereafter be determined from Equation 3 as follow:

$$G = [(I_{we1} + I_{we2}) - \text{Intercept}]/\text{Slope} \qquad \text{Eq. 3}$$

Where $I_{we1}$ is the current measured for the first working electrode at the end of T1;

$I_{we2}$ is the current measured for the second working electrode at the end of T1;

Slope is the value obtained from calibration testing of a batch of test strip of which this particular strip comes from;

Intercept is the value obtained from calibration testing of a batch of test strip of which this particular strip comes from.

From Eq. 3 G=[(1600+1300)−500]/18 and therefore, G=133.33 mg/dL ~133 mg/dL.

It is noted that certain offsets may be provided to the current value Iwe1 and Iwe2 to account for errors or delay time in the electrical circuit of the meter 200. Temperature compensation can also be utilized to ensure that the results are calibrated to a referential temperature such as for example room temperature of about 20 degrees Celsius.

Figure 5:
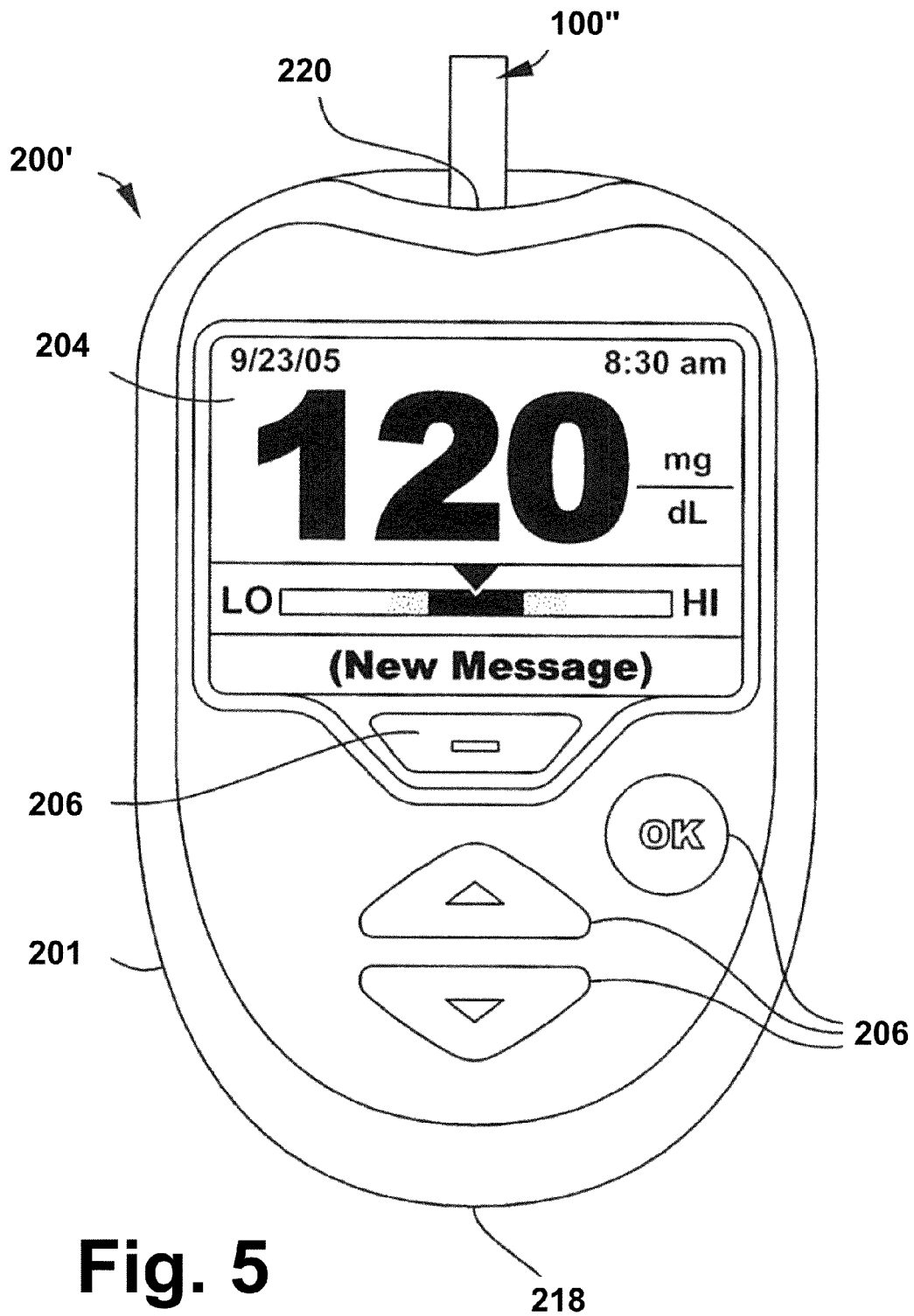
FIG. 5 illustrates yet another alternate measurement system.
Figure 6:
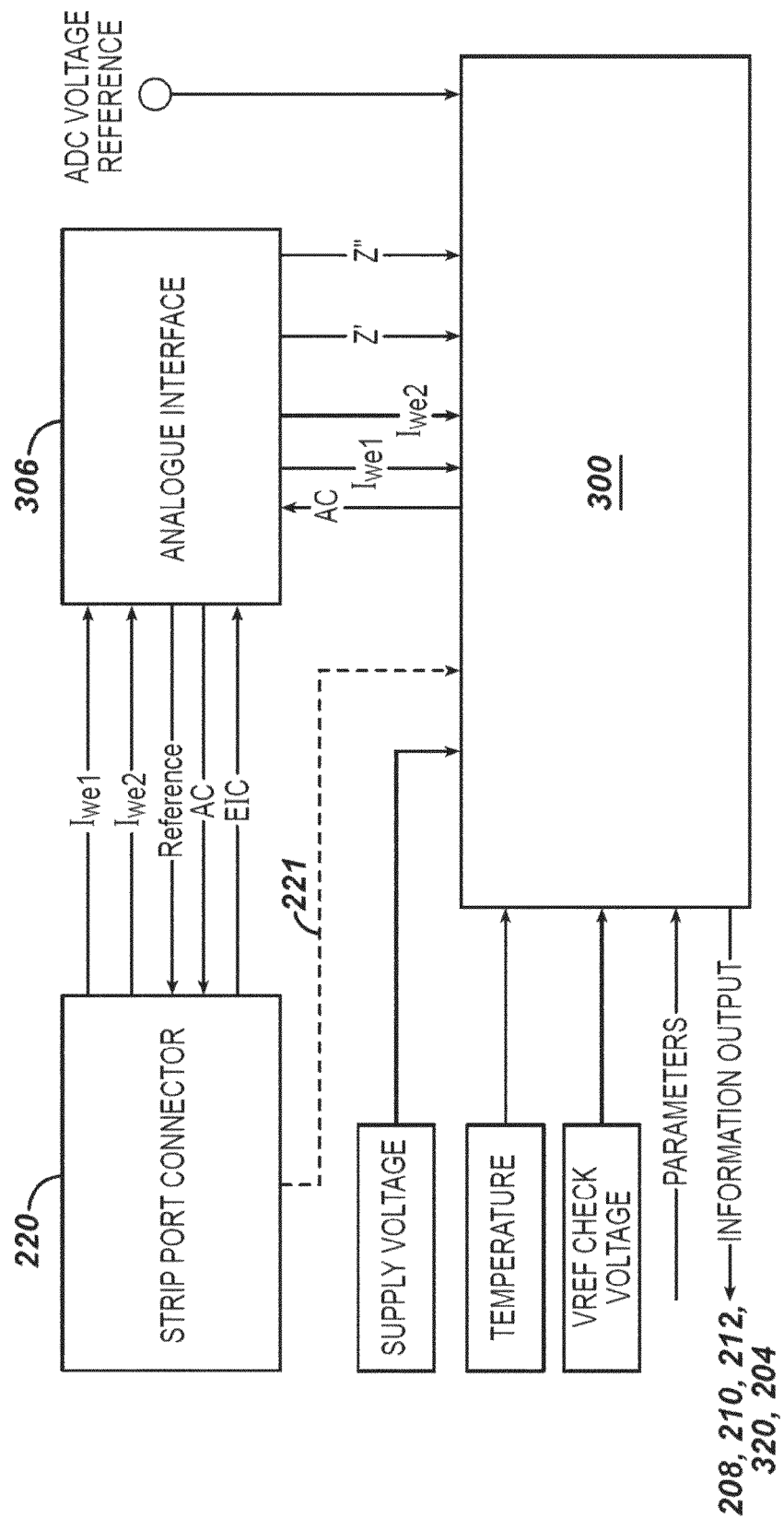
FIG. 6 illustrates in simplified schematic form of the components for the meter of FIG. 5.

FIG. 5 is a simplified depiction of an alternate hand-held test meter 200' and FIG. 6 is a simplified schematic diagram of the components in this alternate test meter 200'. Electrical modeling of a bodily fluid sample (i.e., a whole blood sample) as parallel capacitive and resistive components indicates that when an alternating signal is forced through the bodily fluid sample, the phase shift of the AC signal will be dependent on both the frequency of the AC voltage and the hematocrit, among other physical characteristics of the sample. Moreover, modeling indicates that hematocrit has a relatively minor effect on the phase shift when the frequency of the signal is in the range of approximately 10 kHz to 25 kHz and a maximum effect on the phase shift when the frequency of the signal is in the range of approximately 250 kHz to 500 KHz. Therefore, the hematocrit of a bodily fluid sample can be inferred by, for example, driving AC signals of known frequency through the bodily fluid sample and detecting their phase shift. For example, the phase-shift of a signal with a frequency in the range of 10 kHz to 25 kHz can be used as a reference reading in such a hematocrit measurement while the phase shift of a signal with a frequency in the range of 250 kHz to 500 kHz can be used as the primary measurement.

Referring to FIG. 6, details of a preferred implementation of meter 200' where the same numerals in FIGS. 2 and 6 have a common description. In FIG. 6, a strip port connector 220 is connected to the analogue interface 306 by five lines including an impedance sensing line EIC to receive signals from physical characteristic sensing electrode(s), alternating signal line AC driving signals to the physical characteristic sensing electrode(s), reference line for a reference electrode, and signal sensing lines from respective working electrode 1 and working electrode 2. A strip detection line 221 can also be provided for the connector 220 to indicate insertion of a test strip. The analog interface 306 provides four inputs to the processor 300: (1) real impedance Z'; (2) imaginary impedance Z"; (3) signal sampled or measured from working electrode 1 of the biosensor or $I_{we1}$; (4) signal sampled or measured from working electrode 2 of the biosensor or $I_{we2}$. There is one output from the processor 300 to the interface 306 to drive an oscillating signal AC of any value from 25 kHz to about 250 kHz or higher to the physical characteristic sensing electrodes. A phase differential P (in degrees) can be determined from the real impedance Z' and imaginary impedance Z" where:

$$P = \tan^{-1}\{Z''/Z'\} \quad \text{Eq. 4}$$

and magnitude M (in ohms and conventionally written as |Z|) from line Z' and Z" of the interface 306 can be determined where $$M = \sqrt{(Z')^2 + (Z'')^2} \quad \text{Eq. 5}$$

Figure 7:
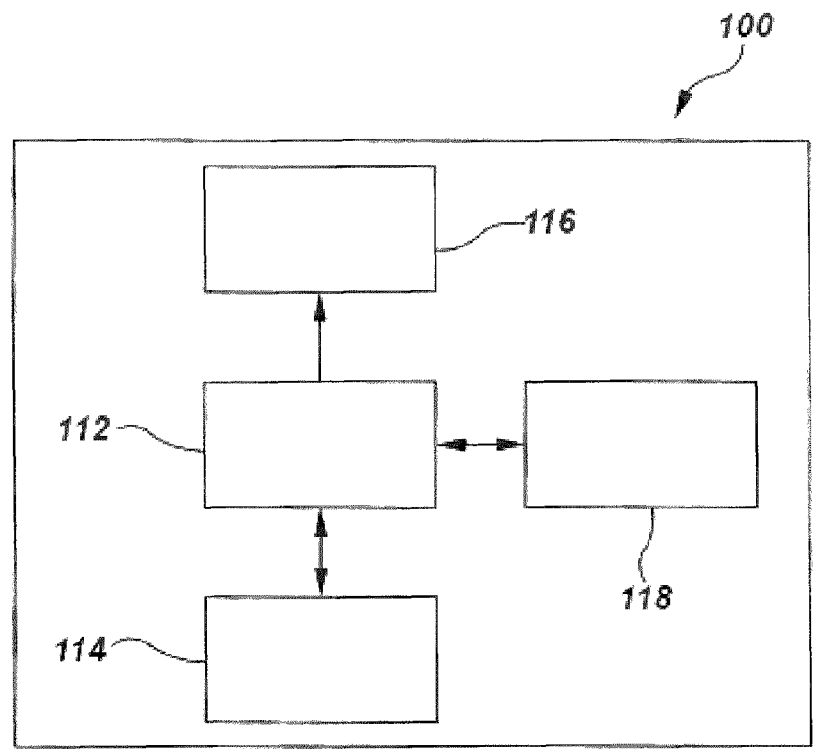
FIG. 7 illustrates in schematic form simplified block diagram of various blocks of the hand-held test meter of FIG. 6.
Figure 8:
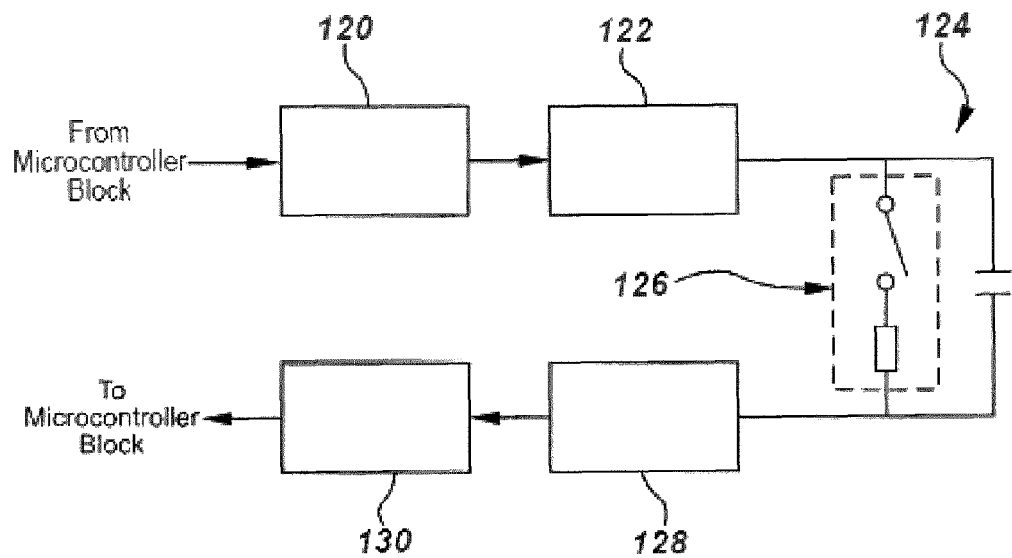
FIG. 8 illustrates a simplified block diagram of an impedance measurement block for the meter of FIG. 5.
Figure 9:
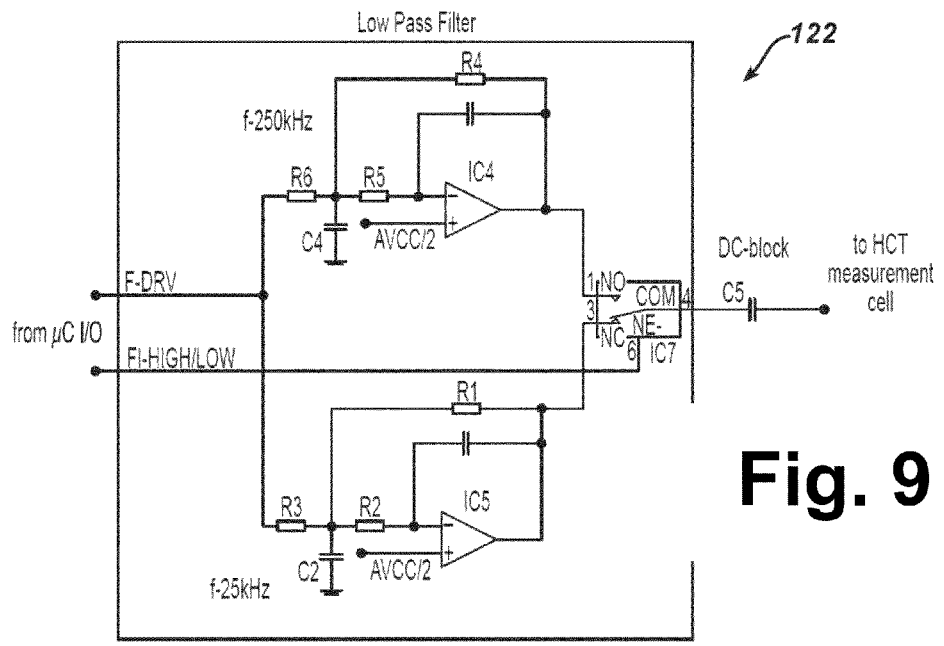
FIG. 9 illustrates a simplified annotated schematic diagram of a dual low pass filter sub-block as can be employed in embodiments of FIG. 5.
Figure 10:
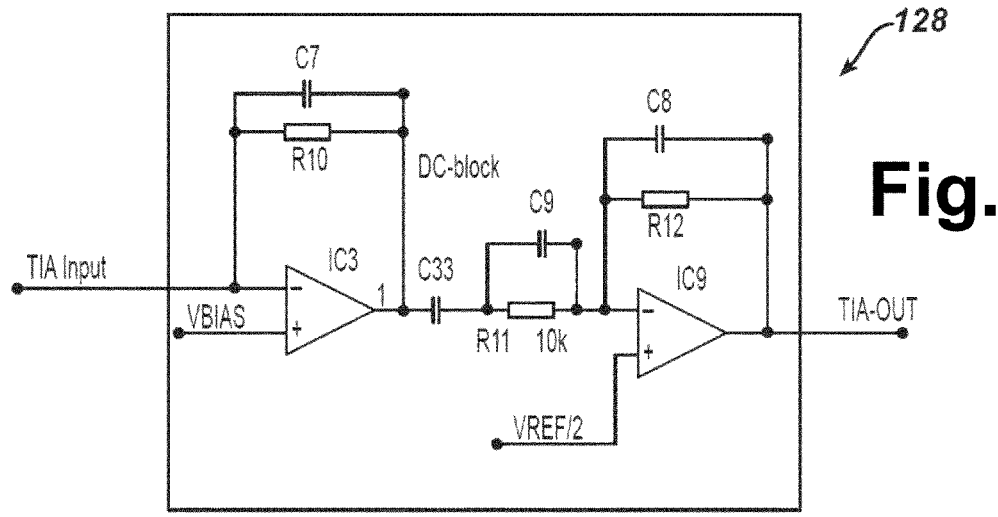
FIG. 10 illustrate a simplified annotated schematic diagram of a transimpedance amplifier (TIA) sub-block as can be employed in embodiments of the present disclosure.
Figure 11:
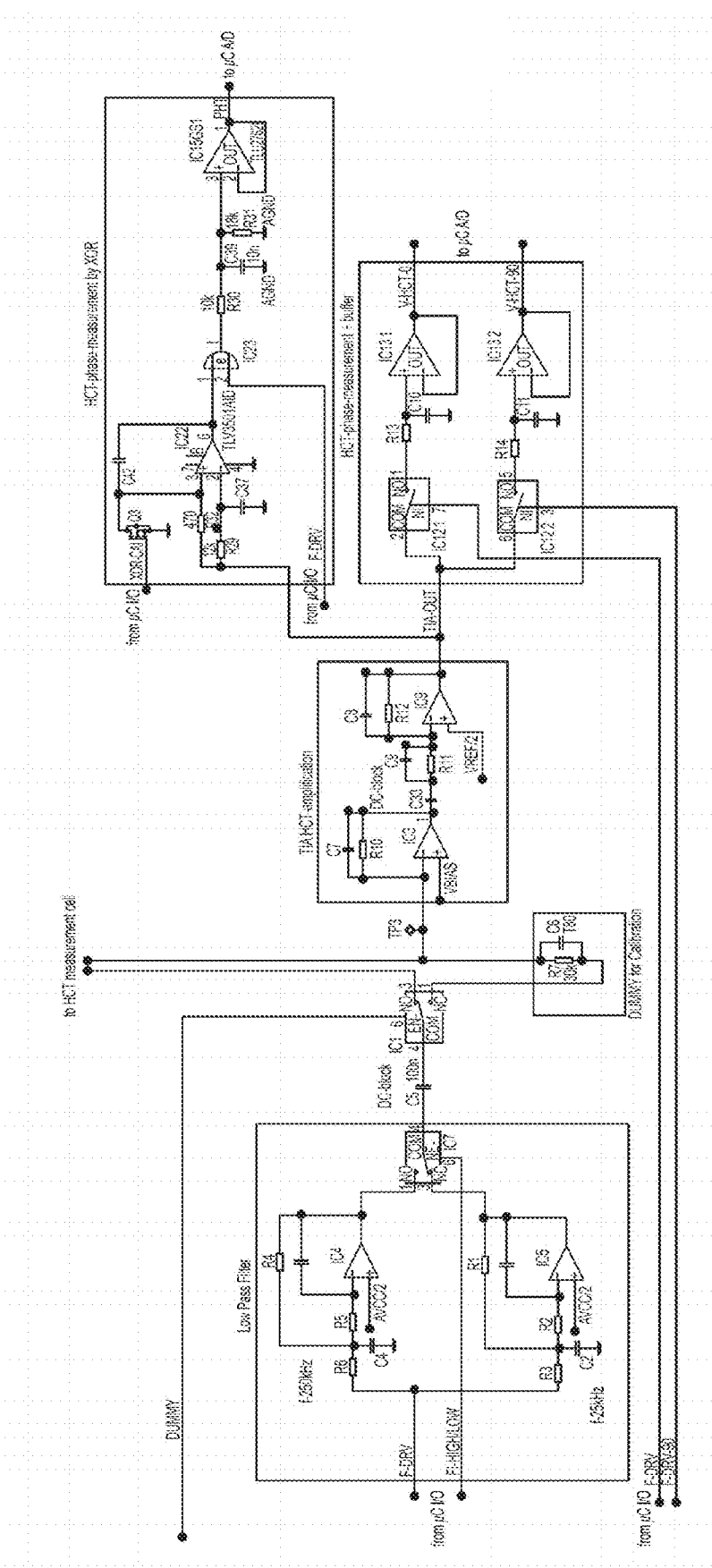
FIG. 11 illustrates a simplified annotated schematic block diagram depicting a dual low pass filter sub-block, a calibration load sub-block, a biosensor sample cell interface sub-block, a transimpedance amplifier sub-block, an XOR phase shift measurement sub-block and a Quadratur DEMUX phase-shift measurement sub-block as can be employed in an impedance measurement block for the system of FIG. 5.

FIG. 7 is a simplified block diagram of various blocks of hand-held test meter 200'. FIG. 8 is a simplified combined block diagram of a phase-shift-based hematocrit measurement block of hand-held test meter 200'. FIG. 9 is a simplified annotated schematic diagram of a dual low pass filter sub-block of hand-held test meter 200'. FIG. 10 is a simplified annotated schematic diagram of a transimpedance amplifier sub-block of hand-held test meter 200'. FIG. 11 is a simplified annotated schematic block diagram of portions of a phase-shift-based hematocrit measurement block of hand-held test meter 200'.

Referring to FIGS. 8 through 13, hand-held test meter 200' includes a display 204, a plurality of user interface buttons 206, a strip port connector 220, a USB interface 218, and a housing 201 (see FIG. 5). Referring to FIG. 7 in particular, hand-held test meter 200' also includes a microcontroller block 112, a phase-shift-based hematocrit measurement block 114, a display control block 116, a memory block 118 and other electronic components (not shown) for applying a test voltage to biosensor (labeled TS in FIG. 5), and also for measuring an electrochemical response (e.g., plurality of test current values) and determining an analyte based on the electrochemical response. To simplify the current descriptions, the figures do not depict all such electronic circuitry.

Display 204 can be, for example, a liquid crystal display or a bi-stable display configured to show a screen image. An example of a screen image may include a glucose concentration, a date and time, an error message, and a user interface for instructing an end user how to perform a test.

Strip port connector 220 is configured to operatively interface with a biosensor TS, such as an electrochemical-based biosensor configured for the determination of glucose in a whole blood sample. Therefore, the biosensor is configured for operative insertion into strip port connector 220 and to operatively interface with phase-shift-based hematocrit measurement block 114 via, for example, suitable electrical contacts.

USB Interface 218 can be any suitable interface known to one skilled in the art. USB Interface 218 is essentially a passive component that is configured to power and provide a data line to hand-held test meter 200'.

Once a biosensor is interfaced with hand-held test meter 200', or prior thereto, a bodily fluid sample (e.g., a whole blood sample) is introduced into a sample chamber of the biosensor. The biosensor can include enzymatic reagents that selectively and quantitatively transform an analyte into another predetermined chemical form. For example, the biosensor can include an enzymatic reagent with ferricyanide and glucose oxidase so that glucose can be physically transformed into an oxidized form.

Memory block 118 of hand-held test meter 200' includes a suitable algorithm and can be configured, along with microcontroller block 112 to determine an analyte based on the electrochemical response of biosensor and the hematocrit of the introduced sample. For example, in the determination of the analyte blood glucose, the hematocrit can be used to compensate for the effect of hematocrit on electrochemically determined blood glucose concentrations.

Microcontroller block 112 is disposed within housing 201 and can include any suitable microcontroller and/or microprocesser known to those of skill in the art. One such suitable microcontroller is a microcontroller commercially available from Texas Instruments, Dallas, Tex. USA and part number MSP430F5138. This microcontroller can generate a square wave of 25 to 250 kHz and a 90 degree phase-shifted wave of the same frequency and, thereby, function as a signal generation s-block described further below. MSP430F5138 also has Analog-to-Digital (A/D) processing capabilities suitable for measuring voltages generated by phase shift based hematocrit measurement blocks employed in embodiments of the present disclosure.

Referring in particular to FIG. 8, phase-shift-based hematocrit measurement block 114 includes a signal generation sub-block 120, a low pass filter sub-block 122, a biosensor sample cell interface sub-block 124, an optional calibration load block 126 (within the dashed lines of FIG. 8), a transimpedance amplifier sub-block 128, and a phase detector sub-block 130.

As described further below, phase-shift-based hematocrit measurement block 114 and microcontroller block 112 are configured to measure the phase shift of a bodily fluid sample in a sample cell of a biosensor inserted in the hand-held test meter by, for example, measuring the phase shift of one or more high frequency electrical signals driven through the bodily fluid sample. In addition, microcontroller block 112 is configured to compute the hematocrit of the bodily fluid based on the measured phase shift. Microcontroller 112 can compute the hematocrit by, for example, employing an A/D converter to measure voltages received from a phase-detector sub-block, convert the voltages into a phase-shift and then employing a suitable algorithm or look-up table to convert the phase-shift into a hematocrit value. Once apprised of the present disclosure, one skilled in the art will recognize that such an algorithm and/or look-up table will be configured to take into account various factors such as strip geometry (including electrode area and sample chamber volume) and signal frequency.

Referring to FIGS. 10 through 13 in particular, signal generation sub-block 120 can be any suitable signal generation block and is configured to generate a square wave (0V to Vref) of a desired frequency. Such a signal generation sub-block can, if desired, be integrated into microcontroller block 112.

The signal generated by signal generation sub-block 120 is communicated to dual low pass filter sub-block 122, which is configured to convert the square wave signal to a sine wave signal of a predetermined frequency. The dual LPF of FIG. 9 is configured to provide both a signal of a first frequency (such as a frequency in the range of 10 kHz to 25 kHz) and a signal of a second frequency (such as a frequency in the range of 250 kHz to 500 kHz) to the biosensor sample cell interface sub-block and a biosensors' sample chamber (also referred to as the HCT measurement cell). Selection of the first and second frequency is accomplished using switch IC7 of FIG. 9. The dual LPF of FIG. 9 includes employs two suitable operational amplifiers (IC4 and IC5) such as the operational amplifier available from Texas Instruments, Dallas, Tex., USA as high-speed, voltage feedback, CMOS operational amplifier part number OPA354.

Referring to FIG. 9, F-DRV represents a square wave input of either a low or high frequency (e.g., 25 kHz or 250 kHz) and is connected to both IC4 and IC5. Signal Fi-HIGH/LOW (from the microcontroller) selects the output of dual low pass filter sub-block 122 via switch IC7. C5 in FIG. 9 is configured to block the operating voltage of dual low pass filter sub-block 122 from the HCT measurement cell.

Although a specific dual LPF is depicted in FIG. 9, dual low pass filter sub-block 122 can be any suitable low pass filter sub-block known to one skilled in the art including, for example, any suitable multiple feedback low pass filter, or a Sallen and Key low pass filter.

The sine wave produced by low pass filter sub-block 122 is communicated to biosensor sample cell interface sub-block 124 where it is driven across the sample cell of the biosensor (also referred to as an HCT measurement cell). Analytical test strip sample cell interface block 124 can be any suitable sample cell interface block including, for example, an interface block configured to operatively interface with the sample cell of the biosensor via first electrode and second electrodes of the biosensor disposed in the sample cell. In such a configuration, the signal can be driven into the sample cell (from the low pass filter sub-block) via the first electrode and picked-up from the sample cell (by the transimpedance amplifier sub-block) via the second electrode as depicted in FIG. 11.

The output signal produced by driving the signal across the sample cell is picked-up by transimpedance amplifier sub-block 128 and converted into a voltage signal for communication to phase detector sub-block 130.

Transimpedance sub-block 128 can be any suitable transimpedance sub-block known to one skilled in the art. FIG. 10 is a simplified annotated schematic block diagram of one such transimpedance amplifier sub-block (based on two OPA354 operational amplifiers, IC3 and IC9). The first stage of TIA sub-block 128 operates at, for example, 400 mV, which limits the AC amplitude to +/−400 mV. The second stage of TIA sub-block 128 operates at Vref/2, a configuration which enables the generation of an output of the full span of the microcontroller A/D inputs. C9 of TIA sub-block 128 serves as a blocking component that only allows an AC sine wave signal to pass.

Phase detector sub-block 130 can be any suitable phase detector sub-block that produces either a digital frequency that can be read back by microcontroller block 112 using a capture function, or an analog voltage that can be read back by microcontroller block 112 using an analog to digital converter. FIG. 11 depicts a schematic that includes two such phase detector sub-blocks, namely an XOR phase detector (in the upper half of FIG. 11 and including IC22 and IC23) and a Quadrature DEMUX phase detector (in the lower half of FIG. 11 and including IC12 and IC13).

FIG. 11 also depicts a calibration load sub-block 126 that includes a switch (IC16) and a dummy load R7 and C6. Calibration load sub-block 126 is configured for the dynamic measurement of a phase offset for the known phase shift of zero degrees produced by resistor R7, thus providing a phase offset for use in calibration. C6 is configured to force a predetermined slight phase shift, e.g. to compensate for phase delays caused by parasitic capacities in the signal traces to the sample cell, or for phase delays in the electrical circuits (LPF and TIA).

The Quadrature DEMUX phase detector circuit of FIG. 11 includes two portions, one portion for a resistive part of the incoming AC signal and one portion for the reactive portion of the incoming AC signal. Use of such two portions enables the simultaneous measurement of both the resistive and reactive portion of the AC signal and a measurement range that covers 0 degrees to 360 degrees. The Quadrature DEMUX circuit of FIG. 11 generates two separate output voltages. One of these output voltages represents the "in phase measurement" and is proportional to the "resistive" part of the AC signal, the other output voltage represents the "Quadrature Measurement" and is proportional to the "reactive part of the signal. The phase shift is calculated as:

$$\Phi = \tan^{-1}(V_{QUAD\text{-}PHASE}/V_{IN\text{-}PHASE}) \qquad \text{Eq. 6.}$$

Such a Quadrature DEMUX phase detector circuit can also be employed to measure the impedance of a bodily fluid sample in the sample cell. It is hypothesized, without being bound, that the impedance could be employed along with the phase-shift, or independently thereof, to determine the hematocrit of the bodily sample. The amplitude of a signal forced through the sample cell can be calculated using the two voltage outputs of the Quadrature DEMUX circuit as follows:

$$\text{Amplitude} = \text{SQR}((V_{QUAD\text{-}PHASE})^2 + (V_{IN\text{-}PHASE})^2) \qquad \text{Eq. 7.}$$

This amplitude can then be compared to an amplitude measured for the known resistor of calibration load block 126 to determine the impedance.

The XOR phase detector portion has a measurement range of 0° to 180°, or alternatively a measurement range of −90° to +90°, depending whether the "Square wave input from μC" is in phase to the sine wave or is set to a 90° phase shift. The XOR phase detector produces an output frequency that is always double the input frequency, however the duty cycle varies. If both inputs are perfectly in phase, the output is LOW, if both inputs are 180° shifted the output is always HIGH. By integrating the output signal (e.g. via a simple RC element) a voltage can be generated that is directly proportional to the phase shift between both inputs.

Once apprised of the present disclosure, one skilled in the art will recognize that phase detector sub-blocks employed in embodiments of the present disclosure can take any suitable form and include, for example, forms that employ rising edge capture techniques, dual edge capture techniques, XOR techniques and synchronous demodulation techniques.

Since low pass filter sub-block 122, transimpedance amplifier sub-block 128 and phase detector sub-block 130 can introduce a residual phase shift into phase-shift-based hematocrit measurement block 114, calibration load block 126 can be optionally included in the phase-shift-based hematocrit measurement block. Calibration load block 126 is configured to be essentially resistive in nature (for example a 33 k-ohm load) and, therefore, induces no phase shift between excitation voltage and generated output signal. Calibration load block 126 is configured to be switched in across the circuit to give a "zero" calibration reading. Once calibrated, the hand-held test meter can measure the phase shift of a bodily fluid sample, subtract the "zero" reading to compute a corrected phase shift and subsequently compute the bodily sample hematocrit based on the corrected phase shift with test strip 100" shown here in FIGS. 12 and 13.

Figure 12:
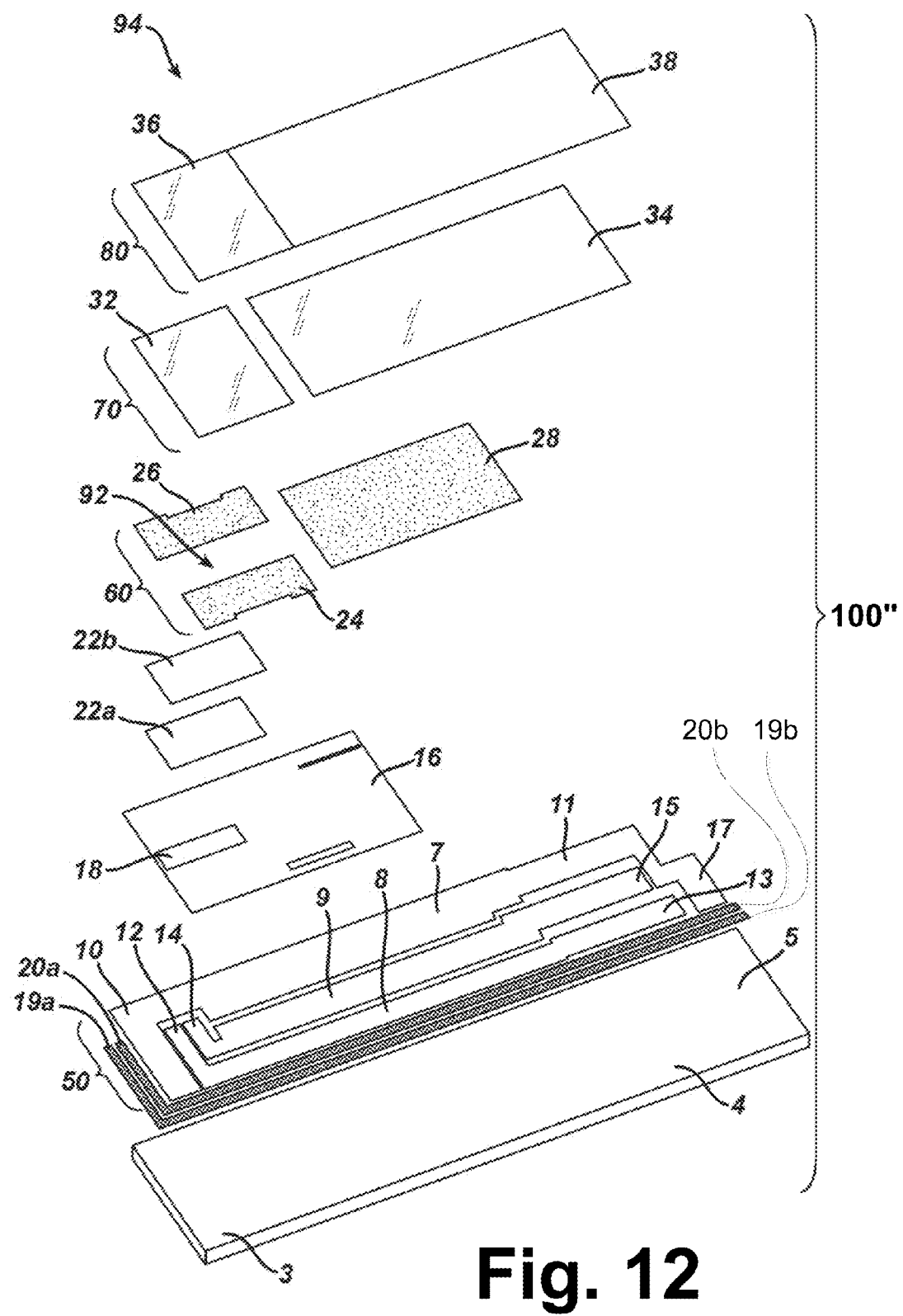
FIG. 12 illustrates a biosensor strip 100" with impedance measurement electrodes for use with the system of FIG. 5.

FIG. 12 is an exemplary exploded perspective view of a test strip 100", which may include seven layers disposed on a substrate 5. The seven layers disposed on substrate 5 can be a first conductive layer 50 (which can also be referred to as electrode layer 50), an insulation layer 16, two overlapping reagent layers 22a and 22b, an adhesive layer 60 which includes adhesive portions 24, 26, and 28, a hydrophilic layer 70, and a top layer 80 which forms a cover 94 for the test strip 100". Test strip 100" may be manufactured in a series of steps where the conductive layer 50, insulation layer 16, reagent layers 22, and adhesive layer 60 are sequentially deposited on substrate 5 using, for example, a screen-printing process. Note that the electrodes 10, 12, and 14) are disposed for contact with the reagent layer 22a and 22b whereas the physical characteristic sensing electrodes 19a and 20a are spaced apart and not in contact with the reagent layer 22. Hydrophilic layer 70 and top layer 80 can be disposed from a roll stock and laminated onto substrate 5 as either an integrated laminate or as separate layers. Test strip 100" has a distal portion 3 and a proximal portion 4 as shown in FIG. 12.

Figure 13:
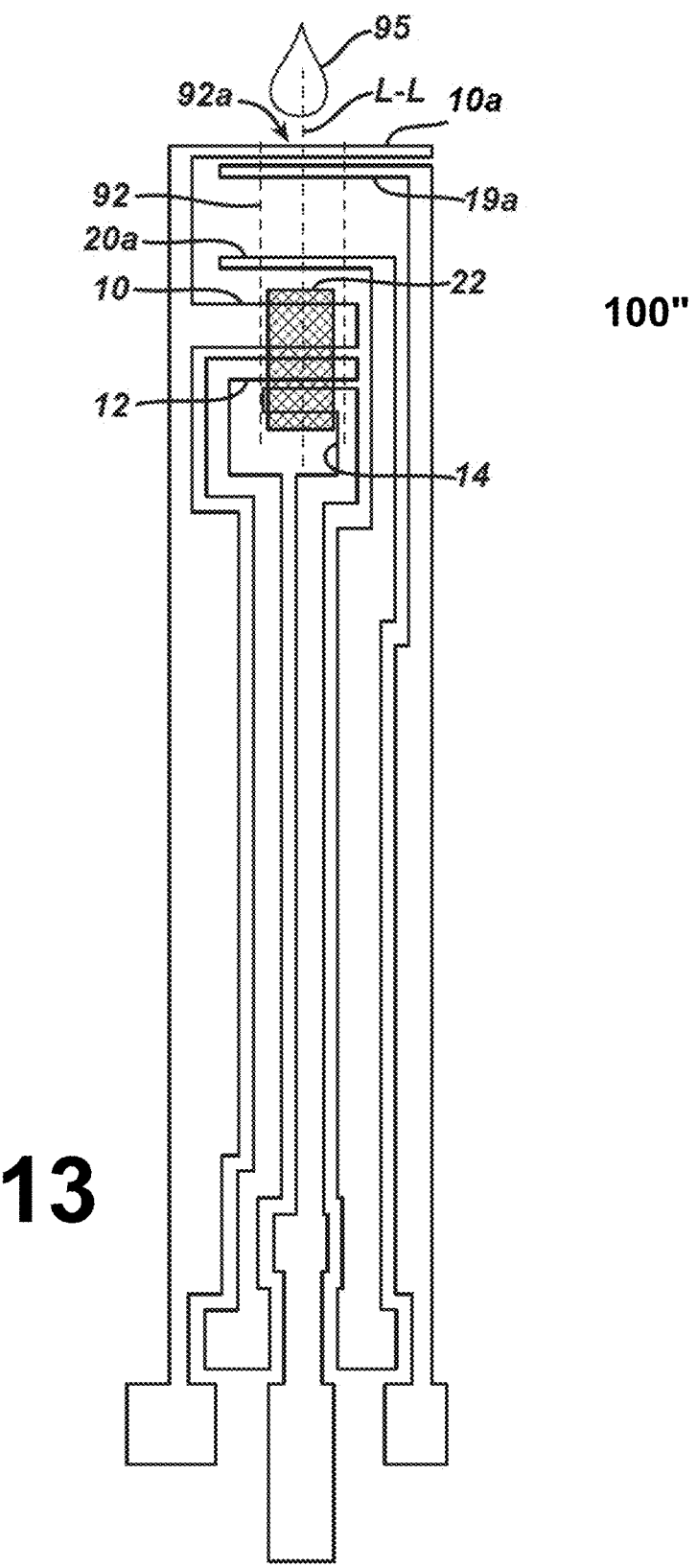
FIG. 13 illustrates a plan view of the strip of FIG. 12.

Test strip 100" may include a sample-receiving chamber 92 through which a physiological fluid sample 95 may be drawn through or deposited (FIG. 13). The physiological fluid sample discussed herein may be blood. Sample-receiving chamber 92 can include an inlet at a proximal end and an outlet at the side edges of test strip 100", as illustrated in FIG. 12. A fluid sample 95 can be applied to the inlet along axis L-L (FIG. 13) to fill a sample-receiving chamber 92 so that glucose can be measured. The side edges of a first adhesive pad 24 and a second adhesive pad 26 located adjacent to reagent layer 22 each define a wall of sample-receiving chamber 92, as illustrated in FIG. 12. A bottom portion or "floor" of sample-receiving chamber 92 may include a portion of substrate 5, conductive layer 50, and insulation layer 16, as illustrated in FIG. 12. A top portion or "roof" of sample-receiving chamber 92 may include distal hydrophilic portion 32, as illustrated in FIG. 12. For test strip 100", as illustrated in FIG. 12, substrate 5 can be used as a foundation for helping support subsequently applied layers. Substrate 5 can be in the form of a polyester sheet such as a polyethylene tetraphthalate (PET) material (Hostaphan PET supplied by Mitsubishi). Substrate 5 can be in a roll format, nominally 350 microns thick by 370 millimeters wide and approximately 60 meters in length.

A conductive layer is required for forming electrodes that can be used for the electrochemical measurement of glucose. First conductive layer 50 can be made from a carbon ink that is screen-printed onto substrate 5. In a screen-printing process, carbon ink is loaded onto a screen and then transferred through the screen using a squeegee. The printed carbon ink can be dried using hot air at about 140° C. The carbon ink can include VAGH resin, carbon black, graphite (KS 15), and one or more solvents for the resin, carbon and graphite mixture. More particularly, the carbon ink may incorporate a ratio of carbon black:VAGH resin of about 2.90:1 and a ratio of graphite:carbon black of about 2.62:1 in the carbon ink.

For test strip 100", as illustrated in FIG. 12, first conductive layer 50 may include a reference electrode 10, a first working electrode 12, a second working electrode 14, third and fourth physical characteristic sensing electrodes 19a and 19b, a first contact pad 13, a second contact pad 15, a reference contact pad 11, a first working electrode track 8, a second working electrode track 9, a reference electrode track 7, and a strip detection bar 17. The physical characteristic sensing electrodes 19a and 20a are provided with respective electrode tracks 19b and 20b. The conductive layer may be formed from carbon ink. First contact pad 13, second contact pad 15, and reference contact pad 11 may be adapted to electrically connect to a test meter. First working electrode track 8 provides an electrically continuous pathway from first working electrode 12 to first contact pad 13. Similarly, second working electrode track 9 provides an electrically continuous pathway from second working electrode 14 to second contact pad 15. Similarly, reference electrode track 7 provides an electrically continuous pathway from reference electrode 10 to reference contact pad 11. Strip detection bar 17 is electrically connected to reference contact pad 11. Third and fourth electrode tracks 19b and 20b connect to the respective electrodes 19a and 20a. A test meter can detect that test strip 100" has been properly inserted by measuring a continuity between reference contact pad 11 and strip detection bar 17, as illustrated in FIG. 12.

In this alternate system (FIGS. 5-14), the microprocessor is configured to: (a) apply a first signal to the plurality of electrodes so that an appropriate sampling time defined by a physical characteristic of a fluid sample is derived and (b) apply a second signal to the plurality of electrodes so that an analyte concentration is determined based on the derived sampling time. For this system, the plurality of electrodes of the test strip or biosensor includes at least two electrodes to measure the physical characteristic and at least two other electrodes to measure the analyte concentration. For example, the at least two electrodes and the at least two other electrodes are disposed in the same chamber provided on the substrate. Alternatively, the at least two electrodes and the at least two other electrodes are disposed in different chambers provided on the substrate. It is noted that for some embodiments, all of the electrodes are disposed on the same plane defined by the substrate. In particular, in some of the embodiments described herein, a reagent is disposed proximate the at least two other electrodes and no reagent is disposed on the at least two electrodes. One feature of note in this system is the ability to provide for an accurate analyte measurement within about 10 seconds of deposition of a fluid sample (which may be a physiological sample) onto the biosensor as part of the test sequence.

The measurement for the physical characteristic can be performed by measuring the impedance of the sample as noted earlier. Once the physical characteristic is determined, an appropriate time instance at which to measure or sample the output signals can be determined by an equation or a look up table using an estimated glucose measurement. Briefly, the appropriate sampling time is given by $$\text{SamplingTime} = x_1 H^{x_2} + x_3 \qquad \text{Eq. 8}$$

where,

"Sampling Time" is designated (for convenience) as a time point from the start of the test sequence at which to sample the output signal of the test strip, H represents the physical characteristic of the sample;

$x_1$ is about 4.3e5;

$x_2$ is about −3.9; and $x_3$ is about 4.8.

Alternatively, the sampling time can be obtained by estimating the glucose value of the sample using a rough guideline of low, medium or high and deriving the appropriate sampling or measuring time from Table A.

TABLE A

| Estimated Analyte | t/Hct (in milliseconds) | Sampling Time Point T for Lo Hct (from start of test sequence, in seconds) | Sampling Time Point T for Mid Hct (from start of test sequence, in seconds) | Sampling Time Point T for High Hct (from start of test sequence, in seconds) |
|---|---|---|---|---|
| Lo-Glucose | 40 | 5.5 | 5 | 4.5 |
| Mid-Glucose | 90 | 6.1 | 5 | 3.9 |
| Hi-Glucose | 110 | 6.3 | 5 | 3.6 |

Other techniques to determine the appropriate batch slope and intercept while holding the sampling time constant can also be utilized as shown and described in U.S. Provisional Patent Application Ser. Nos. 61/581,087 ; 61/581,089 ; 61/581,099 ; and 61/581,100 , all filed on the same day of Dec. 29, 2011, and U.S. Provisional Patent Application Ser. No. 61/654,013 , filed on 31 May 2012, PCT/GB2012/053279 (published as WO2013/098565); PCT/GB2012/053277 (published as WO2013/098564), and PCT/GB2012/053276 (published as WO2013/098563) all International Patent Applications filed on Dec. 28, 2013, all of the applications (provisional and PCT applications) are hereby incorporated by reference as if set forth herein.

Once the appropriate sampling time is determined, the system can now measure or sample the output signal at a specified time point or interval where hematocrit has virtually no effect on the glucose electrochemical transformation. The measurement at the appropriate sampling time (derived from the sensed physical characteristic) to determine glucose concentration is discussed in detail as follow with respect to FIGS. 14A, 14B and 5 below.

Figure 14A:
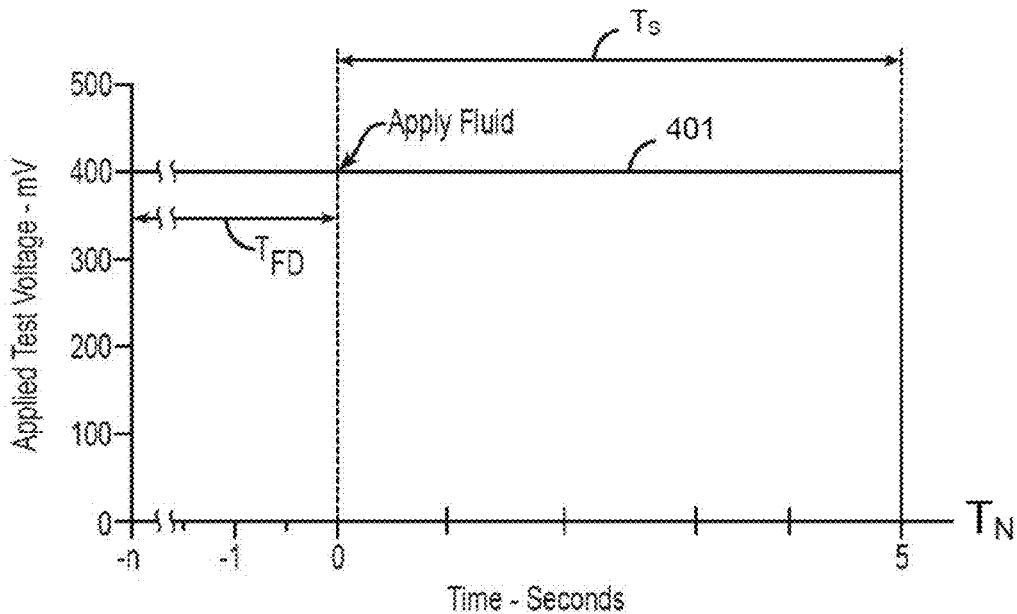
FIG. 14A illustrate the magnitude of signal applied to one electrode during a test sequence.

FIG. 14A is an exemplary chart of a test signal applied to test strip 100" and its variations shown here in FIGS. 12 and 13. Before a fluid sample is applied to the test strip shown in FIGS. 12 and 13, test meter 200' is in a fluid detection mode in which a first test signal of about 400 millivolts is applied between second working electrode and reference electrode. A second test signal of about 400 millivolts is preferably applied simultaneously between first working electrode (e.g., electrode 12 of strip 100") and reference electrode (e.g., electrode 10 of strip 100"). Alternatively, the second test signal may also be applied contemporaneously such that a time instance of the application of the first test signal overlaps with a time interval in the application of the second test voltage. The test meter may be in a fluid detection mode during fluid detection time interval $T_{FD}$ prior to the detection of physiological fluid at starting time at zero. In the fluid detection mode, test meter 200' determines when a fluid is applied to the test strip shown in FIGS. 12 and 13 such that the fluid wets either the first working electrode 12 or second working electrode 14 (or both working electrodes) with respect to reference electrode 10. Once test meter 200' recognizes that the physiological fluid has been applied because of, for example, a sufficient increase in the measured test output signal at either or both of first working electrode 12 and second working electrode 14, test meter 200' assigns a zero second marker at zero time "0" and starts the test time sequence $T_S$. Test meter 200' may sample the current transient output at a suitable sampling rate, such as, for example, every 1 milliseconds to every 100 milliseconds, referenced here as sampling interval "i" in FIG. 14B. Upon the completion of the test time interval $T_S$, the test signal is removed. For simplicity, FIG. 14A only shows the first test signal applied to the test strip shown in FIGS. 12 and 13.

Hereafter, a description of how glucose concentration is determined from the known signal transients (e.g., the measured electrical signal response in nanoamperes as a function of time) that are measured when the test voltages of FIG. 14A are applied to the test strip shown in FIGS. 12 and 13.

Figure 14B:
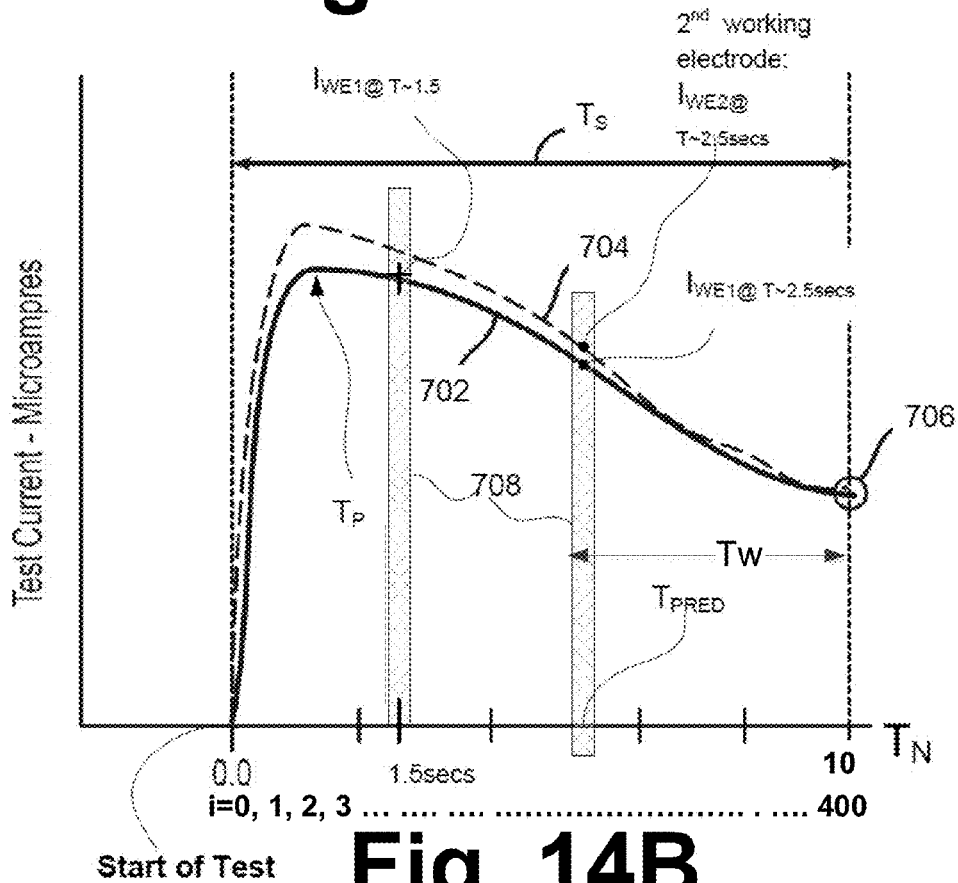
FIG. 14B illustrates the magnitude of the output signal from the electrodes due to the electrochemical reaction during a test measurement sequence.

In FIG. 14A, the first and second test voltages applied to test strip 100" (or its variants described herein) are generally from about +100 millivolts to about +600 millivolts. In one embodiment in which the electrodes include carbon ink and the mediator includes ferricyanide, the test signal is about +400 millivolts. Other mediator and electrode material combinations will require different test voltages, as is known to those skilled in the art. The duration of the test voltages is generally from about 1 to about 10 seconds after a reaction period and is typically about 3 seconds after a reaction period. Typically, test sequence time $T_S$ is measured relative to time $t_0$. As the voltage 401 is maintained in FIG. 14A for the duration of $T_S$, output signals are generated, shown here in FIG. 14B with the output signal transient 702 for the first working electrode 12 being generated starting at zero time and likewise the output signal transient 704 for the second working electrode 14 is also generated with respect to the zero time. The output signals 702 and 704 (from respective working electrodes) are measured or sampled over time instances "t" such that there are approximately 400 measurements (or sampling intervals), depending on the duration of the test sequence. It is noted that while the signal transients 702 and 704 have been placed on the same referential zero point for purposes of explaining the process, in physical term, there is a slight time differential between the two signals due to fluid flow in the chamber towards each of the working electrodes 12 and 14 along axis L-L. However, the output signal transients are sampled and configured in the microcontroller to have the same start time. In FIG. 14B, the output signal transients build up to a peak proximate peak time Tp at which time, the output signal slowly drops off until approximately one of 2.5 seconds or 5 seconds after zero time. At the point 706, approximately at 10 seconds after the start Ts, the output signal for each of the working electrodes 12 and 14 may be measured and added together. Alternatively, the signal from only one of the working electrodes 12 and 14 can be doubled.

Referring back to FIG. 6, the controller 300 drives a signal to measure or sample the output signals $I_E$ from at least one the working electrodes (12 and 14) at any one of a plurality of time instances or positions $T(t)=T_1, T_2, T_3, \ldots T_N$. As can be seen in FIG. 14B, the time position can be any time point or interval "i" in the test sequence $T_S$. For example, the time position at which the output signal is measured can be a single time point $T_{1.5}$ at 1.5 seconds or an interval 708 (e.g., interval~10 milliseconds or more depending on the sampling rate of the system) overlapping the time point $T_{2.8}$ proximate 2.8 seconds.

Output transient signals 702 and 704 can be sampled at the appropriate time (Eq. 8 or Table A) to derive signals $I_{WE1}$ (by summation of each of the output signal $I_{WE1}$ and $I_{WE2}$ or doubling of one of $I_{WE1}$ or $I_{WE2}$) at various time positions during the test sequence. And from knowledge of the batch calibration code offset and batch slope for the particular test strip 100" along with measured magnitude of the output signal at the appropriate sampling time (Eq. 8 or Table A), the analyte (e.g., glucose) concentration is calculated.

Additional details of the techniques to obtain a glucose concentration that is virtually unaffected by hematocrits are shown and described in U.S. Provisional Patent Application Ser. Nos. 61/581,087 ; 61/581,089 ; 61/581,099 ; and 61/581,100 , all filed on the same day of Dec. 29, 2011, and U.S. Provisional Patent Application Ser. No. 61/654,013 , filed on 31 May 2012, PCT/GB2012/053279 (published as WO2013/098565); PCT/GB2012/053277 (published as WO2013/098564), and PCT/GB2012/053276 (published as WO2013/098563) all International Patent Applications filed on Dec. 28, 2013, all of which are hereby incorporated by reference as if set forth herein.

Figure 15B:
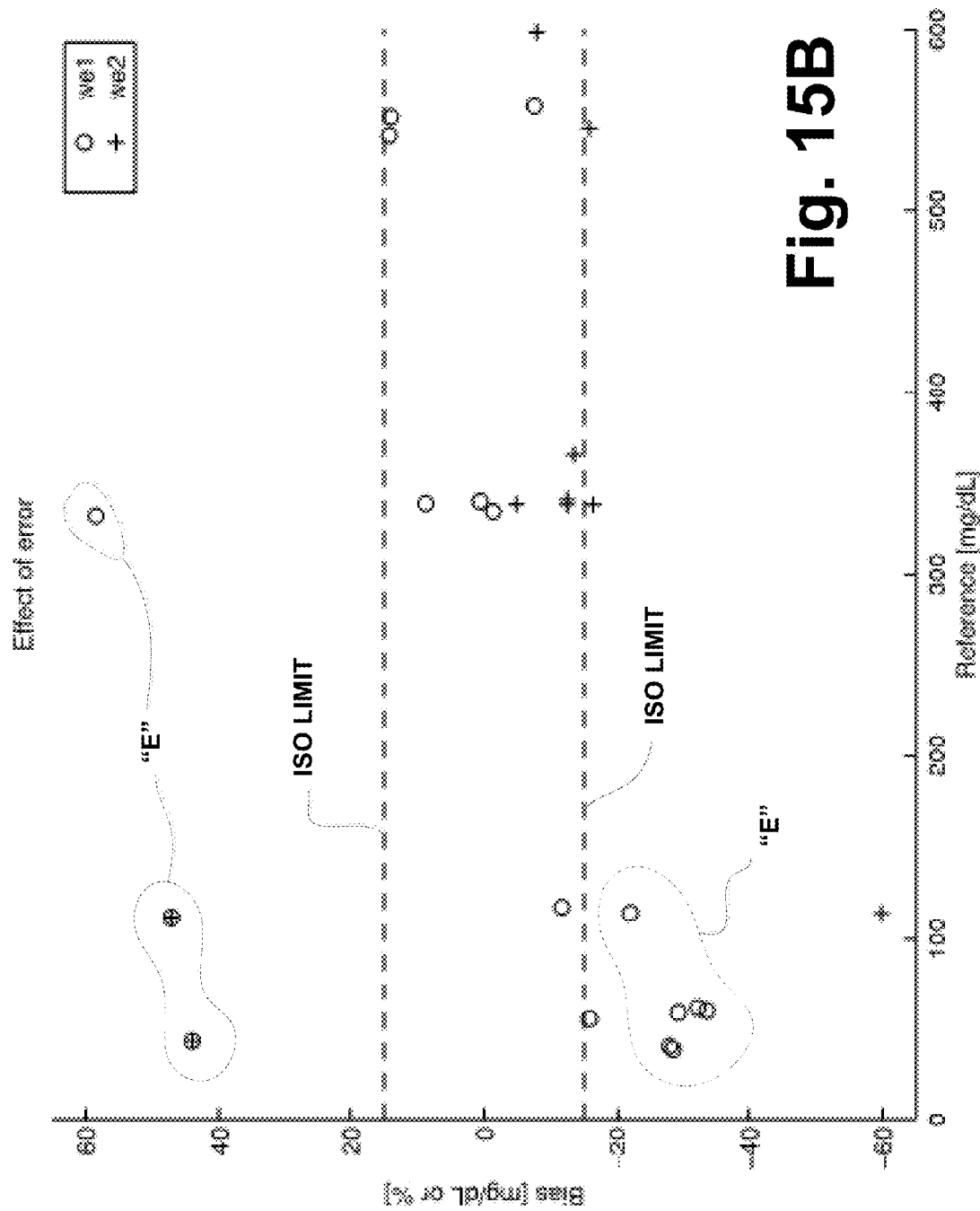
FIG. 15B illustrates graphically the effects of erroneous output signal transients on the final glucose measurement as plotted against ISO limits.

In utilizing our glucose measurement systems to derive a more accurate glucose measurement, we have devised a technique to identify error in the output signal transient. Briefly, other electrochemically active species within the sample (here: patient's blood) may contribute to the output of the signal being sampled. Also material defects leading to geometry changes of the sample chamber may influence the flow of the sample over the working electrodes. This can manifest itself in uneven physical sample flowing (waves or liquid fronts), which may be registered by the sensor as multiple peaks (FIG. 15A) within the current signal over time. If such an event occurs at the time of final assay measurement time, the current recorded may be disproportionally large, which in turn leads to error or bias in the glucose measurement.

The error may occur on either one of the working electrodes independently of the other. By applying our technique to 103,686 output signal transients, we were able to identify 27 output signal transients shown here in FIG. 15A. In FIG. 15A, it can be seen that each of the output signal transients fails to maintain an asymptotic-like trajectory during a predetermined time range (~2 secs to ~14 secs) of the measurement test sequence. In particular, it can be seen that the erroneous signals may have spurious responses, spikes, or drop-offs that are uncharacteristic of the desired electrochemical response during a test measurement sequence.

While the 27 erroneous signals comprise a small proportion of the 103,686 output signal transients (equating to 0.026%), one has to consider the impact of these erroneous output signals. Each of the erroneous output signals picked up would have contributed to a bias or error in excess of 25% to the final glucose measurement, shown here in FIG. 15B as dashed perimeters E. As the erroneous output signals E are outside of the ISO accuracy limits, such output signals are of little or no value to the user. Therefore, it is of significant benefit for the user to have a glucose measurement system that is capable of identifying these types of output signal error and annunciating such error to the user (or aborting the glucose measurement upon such identification).

Hence, we have configured microcontroller 300 (which is coupled to a power source, memory and the plurality of electrodes of the biosensor 100 or 100') so that the microcontroller is programmed with logic process 800 (FIG. 16) to drive a signal, at step 802) to the at least two electrodes when a fluid sample with an glucose is deposited proximate the at least two electrodes (FIGS. 3A and 13) to start a test measurement sequence (FIG. 4A, 4B or 14A and 14B) for an electrochemical reaction of the glucose in the fluid sample with the enzyme. The microcontroller 300 measures, at step 804, an output signal (I(t)) from at least one electrode during the electrochemical reaction over a series of time instances "t" to obtain a magnitude of the output signal for each time instance "t". At step 806, the microcontroller 300 evaluates all of the measured or sampled signals I(t) where "t" is time at each interval "i" from the beginning t(start) of the test window Tw to the end t(end) of the test sequence. The evaluation 806 starts with a query at step 808 to determine if the evaluation is completed to determine if the time "t" is less or equal to the end time t(end). If the query 808 returns a "no", meaning that the time instance "t(t)" for which the output signal I being evaluated is greater than the end t(end) of the test window Tw (which can be from 2 to 15 seconds after test start time) then the controller moves to step 810 calculate the glucose value at step 810. At step 812, the controller will, depending on the prior step (810 or 826), will annunciate the glucose value or an indication of an error in the measurement signals. If the query 808 returns a "yes"; meaning that the time instance "(t)" (where t=interval 1, 2, 3 . . . "i") for which the output signal is being evaluated is less than the test end time, then the controller increments the sampling interval at step 816 to the next time instance in its evaluation of the output signal. At step 816, the controller evaluates the current or instant time point at which the output signal is being evaluated to ensure that the current time point "t" is within a window from the start time to the end time. If the query at step 816 returns a "no" then the controller returns to step 808 otherwise if the query 816 returns a "yes", meaning that the time instance for which the measured output signal is being evaluated is within this window, and the controller determines, at step 818 an output differential ΔI as a difference in the respective magnitudes of the output signal for at least two consecutive time instances ((t) and (t+1) or alternatively (t) and (t−1)) within a predetermined time window Tw from the start t (e.g., i=0 or i=c) to the end t (e.g., i=end or i=d) of the test measurement sequence.

At step 820, if the output differential ΔI is greater than zero then the microcontroller 300 performs two tasks: (1) increment a first index x by one, i.e., x=x+1 and (2) set a second index y value as equal to the sum of a previous value of the second index y and the output differential ΔI, i.e., y=y+ΔI. At query step 824, if the first index x is greater or equal to a first threshold "a" and a second index "y" is greater than a second threshold "b" then controller moves to step 826 to flag or annunciate an error. Otherwise, if the query at step 824 returns a "no" then the system returns to step 808 to determine if the time period is outside the time window from start to end. If query 808 returns a true or yes then the system calculates (described earlier) the glucose value from the output signal at step 810 and at step 812 returns to the main routine and annunciate the glucose value. Assuming that both queries at 824 return respective false or no then there is no error in the output signal(s) and the system may annunciate the glucose measurement calculated at step 810.

As implemented, our technique provides a technical contribution in the art because it takes as little resource as possible from the microcontroller—only four parameters need to be introduced ('a', 'b', along with start time 'c' and end time 'd' of the test sequence) and two variables retained and updated ('x' & 'y' and preferably x~0 and y~0 as initial values). For the system utilizing strip 100 (FIGS. 1-4), Table 1 provides the range of parameters for such system in the utilization of logic process 800 of FIG. 16.

TABLE 1

Parameters

| Parameter | System FIGS. 1-4 |
|---|---|
| First threshold "a" | ≈5 |
| Second threshold "b" [nA] | ≈300 |
| c—Window Start Time of Tw | ≈1 second from start of test sequence |
| d—Window End Time of Tw | ≈5 seconds from start of test sequence |

First threshold 'a' describes the number of consecutive rising current points necessary to trigger the error. Second threshold 'b' defines the relative height of the elevated measurement points (maximum-minimum) necessary to trigger the error. Parameters 'c' and 'd' define the time window in which the error has to occur to merit an error trigger ('c' is the start time, 'd' is the end time for time window Tw).

Figure 16:
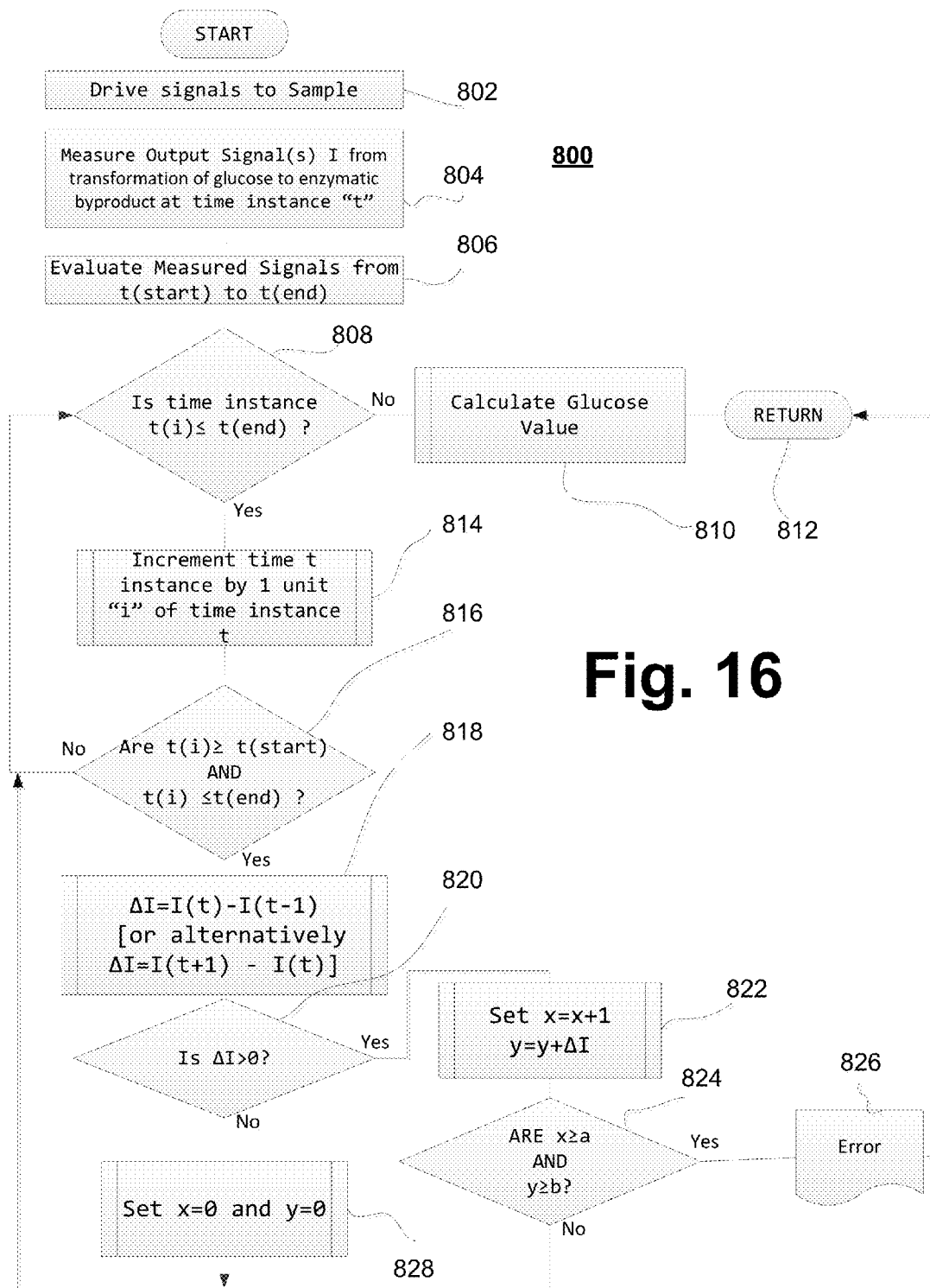
FIG. 16 illustrates a logic diagram to determine whether the output signal during a test measurement sequence is unusable or erroneous as part of the measurement technique employed for the system of FIGS. 1-4 or FIG. 5-14.

For the alternate system of FIGS. 5-14, the parameters utilized in the logic 800 of FIG. 16 are shown below.

TABLE 2

Parameters

| Parameter | System FIGS. 5-14 |
|---|---|
| First threshold "a" | ≈5 |
| Second threshold "b" [nA] | ≈150 |
| c—Window Start Time of Tw | ≈2.5 second from start of test sequence |
| d—Window End Time of Tw | ≈8 seconds from start of test sequence |

With our technique and appropriate parameters being set, an error is triggered only if all three conditions are satisfied (number of points, relative elevation and time window) in either of the system of FIGS. 1-4 or the system of FIGS. 5-14 during a glucose measurement. This makes the technique scalable, which in turns allows finding an appropriate balance between true positives (output signals which trigger the trap, and lead to an inaccurate result) and false positives (output signals which trigger the trap, yet lead to an accurate result). Of the 27 output signal transients identified by our technique in FIG. 15A, 15 out of the 27 are true positives while 12 are false positives (see the points within ISO limits in FIG. 15B). Since the double peak induced by the error is substantial, we deem these 12 output signals as true positives considering that a 56% chance persists of an inaccurate bias being generated, given our preference of erring on the side of caution.

While the invention has been described in terms of particular variations and illustrative figures, those of ordinary skill in the art will recognize that the invention is not limited to the variations or figures described. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well.

What is claimed is:

1. A glucose measurement system comprising:
   a biosensor having a plurality of electrodes including at least two electrodes with an enzyme disposed thereon; and
   a meter including:
      a microcontroller coupled to a power source, memory and the plurality of electrodes of the biosensor and in which the microcontroller is configured to:
         drive a signal to the at least two electrodes when a fluid sample comprising glucose is deposited proximate the at least two electrodes to start a test measurement sequence for an electrochemical reaction of the glucose in the fluid sample with the enzyme;
         measure an output signal from at least one electrode during the electrochemical reaction over a series of time instances to obtain a magnitude of the output signal for each time instance;
         determine an output differential as a difference in the respective magnitudes of the output signal for two consecutive time instances, at least one of the two consecutive time instances being within a predetermined time window during the test measurement sequence;
      if the output differential is greater than zero then
         (1) increment a first index by one and
         (2) set a second index value as equal to
            the sum of a previous value of the second index and the output differential
         and
      if the first index is greater or equal to a first threshold and the second index is greater than a second threshold
         then annunciate an error
         otherwise if one of the two consecutive time instances is outside of the predetermined time window then calculate a glucose value from the output signal and annunciate the glucose value.

2. The system of claim 1, in which the predetermined time window is from about 1 second after a start of a test sequence to about 8 seconds after the start of the test sequence.

3. The system of claim 1, in which the first threshold is about 5 and the second threshold is about 300 nanoamperes.

4. The system of claim 1, in which the predetermined time window is from about 2 seconds after a start of a test sequence to about 8 seconds after the start of the test sequence.

5. The system of claim 1, in which the first threshold is about 5 and the second threshold is about 150.

6. A method of determining a glucose value from a fluid sample with a biosensor having at least two electrodes and reagent disposed thereon and a glucose meter having a microcontroller configured to connect to the biosensor and to a memory and a power source, the method comprising the steps of:
   initiating a start of a test measurement sequence upon deposition of a fluid sample proximate the at least two electrodes of the biosensor;
   applying an input signal to the fluid sample to cause a transformation of glucose into an enzymatic by-product;
   measuring output signal transient from the fluid sample including over a predetermined time window from the start of the test sequence, the measuring including sampling an output signal from at least one electrode during the electrochemical reaction over a series of time instances to obtain a magnitude of the output signal for each time instance;
   determining an output differential as a difference in the respective magnitudes of the output signal for two consecutive time instances, at least one of the two consecutive time instances being within the predetermined time window during the test measurement sequence;
   if the output differential is greater than zero then:
   (1) incrementing a first index by one and
   (2) setting a second index value as equal to the sum of a previous value of the second index and the output differential;
   and
   if the first index is greater or equal to a first threshold and a second index is greater than a second threshold then annunciating an error,
   otherwise if one of the two consecutive time instances is greater than the predetermined time window then calculating a glucose value of the fluid sample and annunciating the glucose value.

7. The method of claim 6, in which the calculating of the glucose value comprises measuring a magnitude of the output signal proximate a predetermined time instance from the start of the test sequence and deriving the glucose value from a first calibration value and a second calibration value.

8. The method of claim 7, in which the deriving comprises utilizing an equation of the form $$G=[I-\text{Intercept}]/\text{Slope}$$

where
   G comprises a glucose value;
   I comprises a summation of the magnitude of the signals measured from each of the electrodes proximate a predetermined time instance;
   Slope comprises a value obtained from calibration testing of a batch of test strip of which this particular strip comes from; and
   Intercept comprises a value obtained from calibration testing of a batch of test strip of which this particular strip comes from.

9. The method of claim 6, in which the predetermined time window is from about 1 second after a start of a test sequence to about 8 seconds after the start of the test sequence.

10. The method of claim 6, in which the first threshold is about 5 and the second threshold comprises about 300 nanoamperes.

11. The method of claim 6, in which the predetermined time window is from about 2 seconds after a start of a test sequence to about 8 seconds after the start of the test sequence.

12. The method of claim 6, in which the first threshold is about 5 and the second threshold is about 150.

* * * * *